(12) United States Patent
Dunkel et al.

(10) Patent No.: US 8,748,471 B2
(45) Date of Patent: Jun. 10, 2014

(54) 2-ALKYL-CYCLOALK(EN)YL-CARBOXAMIDES

(71) Applicant: Bayer CropScience AG, Monheim (DE)

(72) Inventors: Ralf Dunkel, Lyons (FR); Hans-Ludwig Elbe, Wuppertal (DE); Jörg Nico Greul, Leichlingen (DE); Benoit Hartmann, Sainte Foy les Lyon (FR); Herbert Gayer, Monheim (DE); Thomas Seitz, Langenfeld (DE); Ulrike Wachendorff-Neumann, Neuwied (DE); Peter Dahmen, Neuss (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/686,557

(22) Filed: Nov. 27, 2012

(65) Prior Publication Data

US 2013/0172367 A1    Jul. 4, 2013

Related U.S. Application Data

(63) Continuation of application No. 11/721,417, filed as application No. PCT/EP2005/013140 on Dec. 8, 2005, now Pat. No. 8,344,015.

(30) Foreign Application Priority Data

Dec. 11, 2004  (DE) .................. 10 2004 059 725

(51) Int. Cl.
  A61K 31/415   (2006.01)
  C07D 231/00   (2006.01)

(52) U.S. Cl.
  USPC ...... 514/406; 514/365; 514/255.06; 548/200; 548/374.1; 544/406; 549/72; 549/487

(58) Field of Classification Search
  USPC .......... 514/255.06, 365, 406; 548/200, 374.1; 544/406; 549/72, 487
  See application file for complete search history.

(56) References Cited

U.S. PATENT DOCUMENTS

| | | | |
|---|---|---|---|
| 3,547,917 A | 12/1970 | Kulka et al. | |
| 5,330,995 A | 7/1994 | Eicken et al. | |
| 5,416,103 A | 5/1995 | Eicken et al. | |
| 5,438,070 A | 8/1995 | Eicken et al. | |
| 5,922,732 A | 7/1999 | Urch et al. | |
| 6,054,473 A | 4/2000 | Elbe et al. | |
| 6,107,336 A | 8/2000 | Elbe et al. | |
| 6,300,353 B1 | 10/2001 | Hayase et al. | |
| 8,344,015 B2 | 1/2013 | Dunkel et al. | |
| 2002/0061913 A1 | 5/2002 | Urch et al. | |
| 2005/0124815 A1 | 6/2005 | Elbe et al. | |
| 2005/0143428 A1 | 6/2005 | Dunkel et al. | |
| 2009/0105311 A1 | 4/2009 | Dunkel et al. | |
| 2010/0130570 A1 | 5/2010 | Desbordes et al. | |

OTHER PUBLICATIONS

Murakoshi et al. CAS: 61: 54772, 1964.*
Allegretti, M., et al., "One-pot, new stereoselective synthesis of *endo*-tropanamine," *Tetrahedron Letters* 42:4257-4259, Elsevier Science Ltd. (2001).
Crowley, P.J., et al., "The Crocacins: Novel Natural Products as Leads for Agricultural Fungicides," *Chimia* 57:685-691, Swiss Chemical Society (2003).
List, B., et al., "Proline-Catalyzed Asymmetric Aldol reactions between Ketones and α-Unsubstituted Aldehydes," *Organic Letters* 3:573-575, American Chemical Society (2001).
Office Action mailed Oct. 18, 2011, in U.S. Appl. No. 12/452,910, Desbordes, et al., filed Jan. 27, 2010.
Office Action mailed Jan. 30, 2012, in U.S. Appl. No. 11/916,436, Dunkel, et al., filed Nov. 7, 2008.
Mousseron-Canet et al., CAS:50:77583 (1956).
Office Action mailed Nov. 30, 2010, in U.S. Appl. No. 12/452,910, Desbordes, et al., filed Jan. 27, 2010.
Office Action mailed Apr. 22, 2011, in U.S. Appl. No. 12/452,910, Desbordes, et al., filed Jan. 27, 2010.
Office Action mailed Jul. 18, 2011, in U.S. Appl. No. 11/916,436, Dunkel, et al., filed Nov. 7, 2008.
Notice of Allowance mailed Jan. 7, 2000, in U.S. Appl. No. 09/230,160, Elbe, et al., filed Jan. 20, 1999 (now U.S. Patent 6,054,473).
Notice of Allowance mailed Mar. 22, 2000, in U.S. Appl. No. 09/230,198, Elbe, et al., filed Jan. 20, 1999 (now U.S. Patent 6,107,336).
Office Action mailed Dec. 2, 1999, in U.S. Appl. No. 09/230,198, Elbe, et al., filed Jan. 20, 1999 (now U.S. Patent 6,107,336).

* cited by examiner

*Primary Examiner* — Rei-tsang Shiao
(74) *Attorney, Agent, or Firm* — Sterne, Kessler, Goldstein & Fox P.L.L.C.

(57) ABSTRACT

Novel 2-alkylcycloalk(en)ylcarboxamides of the formula (I)

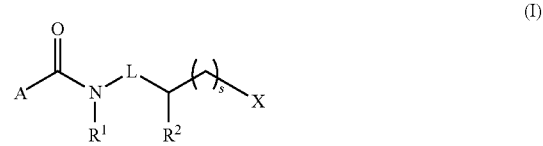

in which
X, s, $R^1$, L, $R^2$ and A are as defined in the description,
a plurality of processes for preparing these compounds and their use for controlling unwanted microorganisms, and also novel intermediates and their preparation.

10 Claims, No Drawings

2-ALKYL-CYCLOALK(EN)YL-CARBOXAMIDES

The present invention relates to novel 2-alkylcycloalk(en)ylcarboxamides, to a plurality of processes for their preparation and to their use for controlling unwanted microorganisms.

It is already known that numerous carboxamides have fungicidal properties (cf., for example, WO 98/03495, WO 98/03486 and EP-A 0 589 313). Thus, some 2-alkylcycloalkylcarboxamides are already known, such as, for example, N-(2-sec-butylcyclohexyl)-2-methyl-4,5-dihydrofuran-3-carboxamide from WO 98/03495, N-[2(2-ethylbutyl)cyclohexyl]-5-fluoro-1,3-dimethyl-1H-pyrazole-4-carboxamide from WO 98/03486 and N-2-sec-butylcyclohexyl)-2-methyl-4-(trifluoromethyl)-1,3-thiazole-5-carboxamide from EP-A 0 589 313. The activity of these compounds is good; however, in some cases, for example at low application rates, it is unsatisfactory.

This invention now provides novel 2-alkylcycloalk(en)ylcarboxamides of the formula (I)

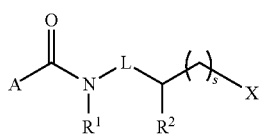

in which
X represents —$CR^3R^4R^5$ or —$SiR^{49}R^{50}R^{51}$,
s represents 1 or 2,
$R^1$ represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^6$, —$CONR^7R^8$ or —$CH_2NR^9R^{10}$,
L represents $L^1$ or $L^2$,
$L^1$ represents $C_3$-$C_7$-cycloalkyl-1,2-ene ($C_3$-$C_7$-cycloalkyl-1,2-diyl) which is optionally mono- to tetrasubstituted by identical or different substituents from the group consisting of fluorine, chlorine, $C_1$-$C_4$-alkyl and $C_1$-$C_4$-haloalkyl,
$L^2$ represents cyclohexenylene (cyclohexenediyl) which is optionally mono- to tetrasubstituted by identical or different substituents from the group consisting of fluorine, chlorine, $C_1$-$C_4$-alkyl and $C_1$-$C_4$-haloalkyl,
$R^2$ represents hydrogen, halogen, $C_1$-$C_4$-alkyl or $C_1$-$C_4$-haloalkyl having 1 to 9 fluorine, chlorine and/or bromine atoms,
$R^3$ represents halogen, $C_1$-$C_8$-alkyl or $C_1$-$C_6$-haloalkyl having 1 to 13 fluorine, chlorine and/or bromine atoms,
$R^4$ represents halogen, $C_1$-$C_8$-alkyl or $C_1$-$C_6$-haloalkyl having 1 to 13 fluorine, chlorine and/or bromine atoms,
$R^5$ represents hydrogen, halogen, $C_1$-$C_8$-alkyl or $C_1$-$C_6$-haloalkyl having 1 to 13 fluorine, chlorine and/or bromine atoms,
$R^3$ and $R^4$ furthermore together with the carbon atom to which they are attached form a 3- to 6-membered carbocyclic or heterocyclic, saturated or unsaturated ring which is optionally substituted by halogen, $C_1$-$C_4$-alkyl, $C_1$-$C_4$-alkoxy, $C_1$-$C_4$-haloalkyl or $C_1$-$C_4$-haloalkoxy,
$R^{49}$ and $R^{50}$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_4$-haloalkyl,
$R^{51}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl,
$R^6$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^7$ and $R^8$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^7$ and $R^8$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^{11}$,
$R^9$ and $R^{10}$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms,
$R^9$ and $R^{10}$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^{11}$,
$R^{11}$ represents hydrogen or $C_1$-$C_6$-alkyl,
A represents the radical of the formula (A1)

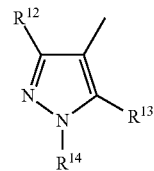

in which
$R^{12}$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl,
$R^{13}$ represents hydrogen, halogen, cyano, $C_1$-$C_4$-alkyl, $C_1$-$C_4$-alkoxy or $C_1$-$C_4$-alkylthio, $R^{14}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, or A represents the radical of the formula (A2)

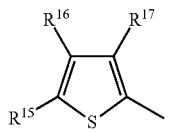
(A2)

in which
$R^{15}$ and $R^{16}$ independently of one another represent hydrogen, halogen, $C_1$-$C_4$-alkyl or $C_1$-$C_4$-haloalkyl having 1 to 5 halogen atoms,
$R^{17}$ represents halogen, cyano or $C_1$-$C_4$-alkyl, or $C_1$-$C_4$-haloalkyl or $C_1$-$C_4$-haloalkoxy having in each case 1 to 5 halogen atoms, or A represents the radical of the formula (A3)

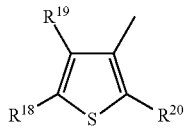
(A3)

in which
$R^{18}$ and $R^{19}$ independently of one another represent hydrogen, halogen, $C_1$-$C_4$-alkyl or $C_1$-$C_4$-haloalkyl having 1 to 5 halogen atoms,
$R^{20}$ represents hydrogen, halogen, $C_1$-$C_4$-alkyl or $C_1$-$C_4$-haloalkyl having 1 to 5 halogen atoms, or A represents the radical of the formula (A4)

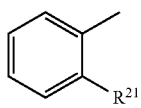
(A4)

in which
$R^{21}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, or A represents the radical of the formula (A5)

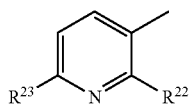
(A5)

in which
$R^{22}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms,
$R^{23}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, or A represents the radical of the formula (A6)

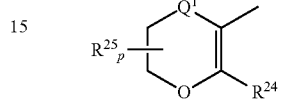
(A6)

in which
$R^{24}$ represents $C_1$-$C_4$-alkyl or $C_1$-$C_4$-haloalkyl having 1 to 5 halogen atoms,
$R^{25}$ represents $C_1$-$C_4$-alkyl,
$Q^1$ represents S (sulphur), O (oxygen), SO, $SO_2$ or $CH_2$,
p represents 0, 1 or 2, where $R^{25}$ represents identical or different radicals if p represents 2, or A represents the radical of the formula (A7)

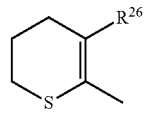
(A7)

in which
$R^{26}$ represents $C_1$-$C_4$-alkyl or $C_1$-$C_4$-haloalkyl having 1 to 5 halogen atoms, or A represents the radical of the formula (A8)

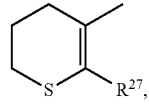
(A8)

in which
$R^{27}$ represents $C_1$-$C_4$-alkyl or $C_1$-$C_4$-haloalkyl having 1 to 5 halogen atoms, or A represents the radical of the formula (A9)

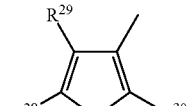
(A9)

in which
$R^{28}$ and $R^{29}$ independently of one another represent hydrogen, halogen, amino, $C_1$-$C_4$-alkyl or $C_1$-$C_4$-haloalkyl having 1 to 5 halogen atoms, $R^{20}$ represents hydrogen, halogen, $C_1$-$C_4$-alkyl or $C_1$-$C_4$-haloalkyl having 1 to 5 halogen atoms, or A represents the radical of the formula (A10)

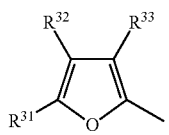
(A10)

in which $R^{31}$ and $R^{32}$ independently of one another represent hydrogen, halogen, amino, nitro, $C_1$-$C_4$-alkyl or $C_1$-$C_4$-haloalkyl having 1 to 5 halogen atoms, $R^{33}$ represents hydrogen, halogen, $C_1$-$C_4$-alkyl or $C_1$-$C_4$-haloalkyl having 1 to 5 halogen atoms, or A represents the radical of the formula (A11)

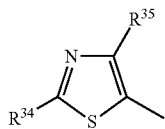
(A11)

in which $R^{34}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{35}$ represents halogen, $C_1$-$C_4$-alkyl or $C_1$-$C_4$-haloalkyl having 1 to 5 halogen atoms, or A represents the radical of the formula (A12)

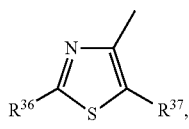
(A12)

in which $R^{36}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{37}$ represents halogen, $C_1$-$C_4$-alkyl or $C_1$-$C_4$-haloalkyl having 1 to 5 halogen atoms, or A represents the radical of the formula (A13)

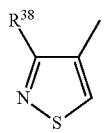
(A13)

in which $R^{38}$ represents halogen, $C_1$-$C_4$-alkyl or $C_1$-$C_4$-haloalkyl having 1 to 5 halogen atoms, or A represents the radical of the formula (A14)

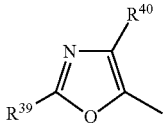
(A14)

in which $R^{39}$ represents hydrogen or $C_1$-$C_4$-alkyl $R^{40}$ represents halogen or $C_1$-$C_4$-alkyl, or A represents the radical of the formula (A15)

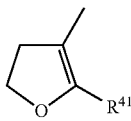
(A15)

in which $R^{41}$ represents $C_1$-$C_4$-alkyl or $C_1$-$C_4$-haloalkyl having 1 to 5 halogen atoms, or A represents the radical of the formula (A16)

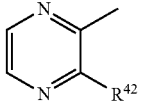
(A16)

in which $R^{42}$ represents hydrogen, halogen, $C_1$-$C_4$-alkyl or $C_1$-$C_4$-haloalkyl having 1 to 5 halogen atoms, or A represents the radical of the formula (A17)

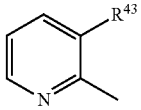
(A17)

in which $R^{43}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, or A represents the radical of the formula (A18)

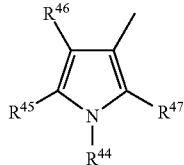
(A18)

in which
$R^{44}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{45}$ represents hydrogen, halogen, $C_1$-$C_4$-alkyl or $C_1$-$C_4$-haloalkyl having 1 to 5 halogen atoms, $R^{46}$ represents hydrogen, halogen, cyano, $C_1$-$C_4$-alkyl or $C_1$-$C_4$-haloalkyl having 1 to 5 halogen atoms, $R^{47}$ represents hydrogen, halogen, $C_1$-$C_4$-alkyl or $C_1$-$C_4$-haloalkyl having 1 to 5 halogen atoms, or A represents the radical of the formula (A19)

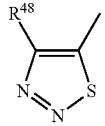
(A19)

in which
$R^{48}$ represents $C_1$-$C_4$-alkyl.

Furthermore, it has been found that 2-alkylcycloalk(en)ylcarboxamides of the formula (I) are obtained when
(a) carboxylic acid derivatives of the formula (II)

(II)

in which
A is as defined above and
$X^1$ represents halogen or hydroxyl,
are reacted with aniline derivatives of the formula (III)

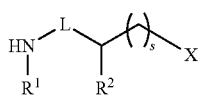
(III)

in which X, s, $R^1$, L and $R^2$ are as defined above, if appropriate in the presence of the catalyst, if appropriate in the presence of a condensing agent, if appropriate in the presence of an acid binder and if appropriate in the presence of a diluent, or (b) 2-alkylcycloalk(en)ylcarboxamides of the formula (I-a)

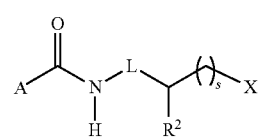
(I-a)

in which X, s, L, $R^2$ and A are as defined above,
are reacted with halides of the formula (IV)

$R^{14}$—$X^2$ (IV)

in which
$R^{14}$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^6$, —CONR$^7$R$^8$ or —CH$_2$NR$^9$R$^{10}$, $R^6$, $R^7$, $R^8$, $R^9$ and $R^{10}$ are as defined above,
$X^2$ represents chlorine, bromine or iodine,
in the presence of a base and in the presence of a diluent.

Finally, it has been found that the novel 2-alkylcycloalk(en)ylcarboxamides of the formula (I) have very good microbicidal properties and can be used for controlling unwanted microorganisms both in crop protection and in the protection of materials.

If appropriate, the compounds according to the invention can be present as mixtures of different possible isomeric forms, in particular of stereoisomers, such as, for example, E and Z, threo and erythro, and also optical isomers, and, if appropriate, also in the form of tautomers. What is claimed are both the E and the Z isomers, and the threo and erythro and also the optical isomers, any mixtures of these isomers and the possible tautomeric forms.

The formula (I) provides a general definition of the 2-alkylcycloalk(en)ylcarboxamides according to the invention. Preferred radical definitions of the formulae mentioned above and below are indicated below. These definitions apply to the end products of the formula (I) and likewise to all intermediates.

X preferably represents —CR$^3$R$^4$R$^5$.
X furthermore preferably represents —SiR$^{49}$R$^{50}$R$^{51}$.
s preferably represents 1.
s furthermore preferably represents 2.
s particularly preferably represents 1.
$R^1$ preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms: or —C(=O)C(=O)$R^6$, —CONR$^7$R$^8$ or —CH$_2$NR$^9$R$^{10}$.

$R^1$ particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$—CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^6$, —CONR$^7$R$^8$ or —CH$_2$NR$^9$R$^{10}$.

$R^1$ very particularly preferably represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

L preferably represents $L^1$.

$L^1$ preferably represents one of the groups below

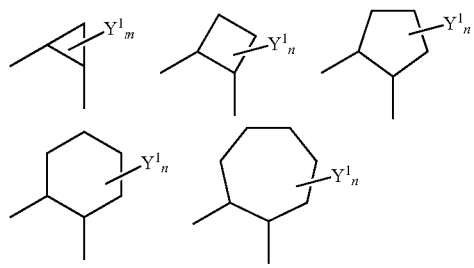

in which
m represents 0, 1 or 2,
n represents 0, 1, 2, 3, or 4, $Y^1$ represents fluorine, chlorine, methyl, ethyl, n- or isopropyl, n-, iso-, sec- or tert-butyl, trifluoromethyl or difluoromethyl, where the radicals $Y^1$ may be identical or different if m or n is greater than 1.

$L^1$ particularly preferably represents one of the groups below

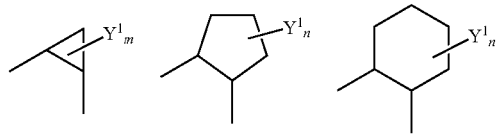

in which
m represents 0, 1 or 2,
n represents 0, 1, 2, 3, or 4,
$Y^1$ represents fluorine, chlorine, methyl, ethyl, n- or isopropyl, n-, iso-, sec- or tert-butyl, trifluoromethyl or difluoromethyl, where the radicals $Y^1$ may be identical or different if m or n is greater than 1.

L furthermore preferably represents $L^2$.

$L^2$ preferably represents cyclohexenylene (cyclohexenediyl) which is optionally mono- to tetra-substituted by identical or different substituents from the group consisting of fluorine, chlorine, methyl, ethyl, n- or isopropyl, n-, iso-, sec- or tert-butyl, trifluoromethyl and difluoromethyl and where the double bond may be in the 1,2-position, 2,3-position, 3,4-position, 4,5-position or 5,6-position.

$L^2$ particularly preferably represents the group

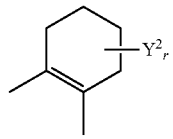

in which
r represents 0 or 1,
$Y^2$ represents fluorine, chlorine or methyl.

$R^2$ preferably represents hydrogen, fluorine, chlorine, methyl, ethyl, n- or isopropyl, or represents methyl, ethyl, n- or isopropyl, n-, iso-, sec- or tert-butyl, each of which is mono- or polysubstituted by identical or different substituents from the group consisting of fluorine, chlorine and bromine.

$R^1$ particularly preferably represents hydrogen, fluorine, chlorine, methyl, ethyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl 2,2,2-trifluoroethyl, 2-chloro-2-fluoroethyl, 2-chloro-2,2-difluoroethyl, 2-dichloro-2-fluoroethyl, 2,2,2-trichloroethyl, 1-chlorobutyl, heptafluoro-n-propyl or heptafluoro-isopropyl.

$R^2$ very particularly preferably represents hydrogen, methyl, ethyl or trifluoromethyl.

$R^2$ especially preferably represents hydrogen or methyl.

$R^3$ preferably represents fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^3$ particularly preferably represents fluorine, chlorine, methyl, ethyl, n- or isopropyl, n-, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^3$ very particularly preferably represents chlorine, methyl, ethyl, isopropyl or trifluoromethyl.

$R^4$ preferably represents fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^4$ particularly preferably represents fluorine, chlorine, methyl, ethyl, n- or isopropyl, n-, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^4$ very particularly preferably represents chlorine, methyl, ethyl, isopropyl or trifluoromethyl.

$R^5$ preferably represents hydrogen, fluorine, chlorine, bromine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^5$ particularly preferably represents hydrogen, fluorine, chlorine, methyl, ethyl, n- or isopropyl, n-, iso-, sec- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-dichloro-2-fluoroethyl, 2,2,2-trichloroethyl, 1-chlorobutyl, heptafluoro-n-propyl or heptafluoroisopropyl.

$R^5$ very particularly preferably represents hydrogen, chlorine, methyl, ethyl, isopropyl or trifluoromethyl.

$R^3$ and $R^4$ furthermore preferably together with the carbon atom to which they are attached form a 3- to 6-membered carbocyclic or heterocyclic saturated or unsaturated ring which is optionally substituted by halogen, methyl, ethyl, methoxy, trifluoromethyl or trifluoromethoxy, $R^3$ and $R^4$ furthermore very particularly preferably together with the carbon atom to which they are attached form a 3-, 5- or 6-membered carbocyclic saturated ring which is optionally substituted by methyl, ethyl or trifluoromethyl, $R^3$ and $R^4$ furthermore very particularly preferably together with the carbon atom to which they are attached form a 6-membered carbocyclic unsaturated ring which is optionally substituted by halogen, methyl, ethyl, methoxy, trifluoromethyl or trifluoromethoxy.

$R^{49}$ and $R^{50}$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^{49}$ and $R^{50}$ independently of one another particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^{49}$ and $R^{50}$ independently of one another very particularly preferably represent methyl, methoxy, methoxymethyl or methylthiomethyl.

$R^{49}$ and $R^{50}$ especially preferably each represent methyl.

$R^{51}$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^{51}$ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^{51}$ very particularly preferably represents methyl, ethyl, n- or isopropyl, iso- or tert-butyl, methoxy, isopropoxy, iso- or tert-butoxy, methoxymethyl, methylthiomethyl or phenyl.

$R^{51}$ especially preferably represents methyl, ethyl, n- or isopropyl, iso- or tert-butyl, methoxy, isopropoxy, iso- or tert-butoxy.

$R^{51}$ most preferably represents methyl.

$R^6$ preferably represents hydrogen, $C_1$-$C_6$-alkyl, $C_1$-$C_4$-alkoxy, $C_1$-$C_3$-alkoxy-$C_1$-$C_3$-alkyl, $C_1$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^6$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^7$ and $R^8$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^7$ and $R^8$ furthermore together with the nitrogen atom to which they are attached preferably form a saturated heterocycle which is optionally mono- to tetrasubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and $NR^{11}$.

$R^7$ and $R^8$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl cyclopentyl, cyclohexyl; trifluoromethyl, trichloromethyl, trifluoroethyl, trifluoromethoxymethyl.

$R^7$ and $R^8$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted at the second nitrogen atom by $R^{11}$.

$R^9$ and $R^{10}$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^9$ and $R^{10}$ furthermore together with the nitrogen atom to which they are attached preferably form a saturated heterocycle which is optionally mono- or polysubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and $NR^{11}$.

$R^9$ and $R^{10}$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^9$ and $R^{10}$ furthermore together with the nitrogen atom to which they are attached particularly preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted at the second nitrogen atom by $R^{11}$.

$R^{11}$ preferably represents hydrogen or $C_1$-$C_4$-alkyl.

$R^{11}$ particularly preferably represents hydrogen, methyl, ethyl, n- or isopropyl, n-, iso-, sec- or tert-butyl.

A preferably represents one of the radicals A1, A2, A3, A4, A5, A6, A9, A10, A11, A12, A16, A17 or A18.

A particularly preferably represents one of the radicals A1, A2, A3, A4, A5, A6, A9, A11, A16, A17, A18.

A very particularly preferably represents the radical A1.

A furthermore very particularly preferably represents the radical A2.

A furthermore very particularly preferably represents the radical A3.

A furthermore very particularly preferably represents the radical A4.

A furthermore very particularly preferably represents the radical A5.

A furthermore very particularly preferably represents the radical A6.

A furthermore very particularly preferably represents the radical A9.

A furthermore very particularly preferably represents the radical A11.

A furthermore very particularly preferably represents the radical A16.

A furthermore very particularly preferably represents the radical A17.

A furthermore very particularly preferably represents the radical A18.

$R^{12}$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

$R^{12}$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^{12}$ very particularly preferably represents hydrogen, fluorine, chlorine, bromine, iodine, methyl, isopropyl, monofluoromethyl, monofluoroethyl, difluoromethyl, trifluoromethyl, difluorochloromethyl or trichloromethyl.

$R^{13}$ especially preferably represents methyl, difluoromethyl, trifluoromethyl or 1-fluoroethyl.

$R^{13}$ preferably represents hydrogen, fluorine, chlorine, bromine, iodine, methyl, ethyl, methoxy, ethoxy, methylthio or ethylthio.

$R^{13}$ particularly preferably represents hydrogen, fluorine, chlorine, bromine, iodine or methyl.

$R^{13}$ very particularly preferably represents hydrogen, fluorine, chlorine or methyl.

$R^{14}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{14}$ particularly preferably represents hydrogen, methyl, ethyl, isopropyl, trifluoromethyl, difluoromethyl, hydroxymethyl, hydroxyethyl or phenyl.

$R^{14}$ very particularly preferably presents hydrogen, methyl, trifluoromethyl or phenyl.

$R^{14}$ especially preferably represents methyl.

$R^{15}$ and $R^{16}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{15}$ and $R^{16}$ independently of one another particularly preferably represent hydrogen, fluorine, chlorine, bromine, methyl, ethyl, difluoromethyl, trifluoromethyl, difluorochloromethyl or trichloromethyl.

$R^{15}$ and $R^{16}$ independently of one another very particularly preferably represent hydrogen, fluorine, chlorine, bromine, methyl, ethyl, difluoromethyl, trifluoromethyl or trichloromethyl.

$R^{15}$ and $R^{16}$ especially preferably each represent hydrogen.

$R^{17}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{17}$ particularly preferably represents fluorine, chlorine, bromine, cyano, methyl, trifluoromethyl, trifluoromethoxy, difluoromethoxy, difluorochloromethoxy or trichloromethoxy.

$R^{17}$ very particularly preferably represents fluorine, chlorine, bromine, iodine, methyl, trifluoromethyl or trifluoromethoxy.

$R^{17}$ especially preferably represents methyl.

$R^{18}$ and $R^{19}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{18}$ and $R^{19}$ independently of one another particularly preferably represent hydrogen, fluorine, chlorine, bromine, methyl, ethyl, difluoromethyl, trifluoromethyl, difluorochloromethyl or trichloromethyl.

$R^{18}$ and $R^{19}$ independently of one another very particularly preferably represent hydrogen, fluorine, chlorine, bromine, methyl, ethyl, difluoromethyl, trifluoromethyl or trichloromethyl.

$R^{18}$ and $R^{19}$ especially preferably each represent hydrogen.

$R^{20}$ preferably represents hydrogen, fluorine, chlorine, bromine, methyl, ethyl or $C_1$-$C_2$-haloalkyl having 1 to 5 fluorine, chlorine and/or bromine atoms.

$R^{20}$ particularly preferably represents hydrogen, fluorine, chlorine, bromine, iodine, methyl or trifluoromethyl.

$R^{20}$ very particularly preferably represents methyl.

$R^{21}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{21}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{21}$ very particularly preferably represents hydrogen, fluorine, chlorine, bromine, iodine, methyl, difluoromethyl, trifluoromethyl or trichloromethyl.

$R^{21}$ especially preferably represents iodine, methyl, difluoromethyl or trifluoromethyl.

$R^{22}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{22}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{22}$ very particularly preferably represents fluorine, chlorine, bromine, iodine, methyl, trifluoromethyl, difluoromethyl or trichloromethyl.

$R^{23}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{23}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{23}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{23}$ especially preferably represents hydrogen.

$R^{24}$ preferably represents methyl, ethyl or $C_1$-$C_2$-haloalkyl having 1 to 5 fluorine, chlorine and/or bromine atoms.

$R^{24}$ particularly preferably represents methyl, ethyl, trifluoromethyl, difluoromethyl, difluorochloromethyl or trichloromethyl.

$R^{25}$ preferably represents methyl or ethyl.

$R^{25}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{26}$ preferably represents methyl, ethyl or $C_1$-$C_2$-haloalkyl having 1 to 5 fluorine, chlorine and/or bromine atoms.

$R^{26}$ particularly preferably represents methyl, ethyl, trifluoromethyl, difluoromethyl, difluorochloromethyl or trichloromethyl.

$R^{26}$ very particularly preferably represents methyl, trifluoromethyl, difluoromethyl or trichloromethyl.

$R^{27}$ preferably represents methyl, ethyl or $C_1$-$C_2$-haloalkyl having 1 to 5 fluorine, chlorine and/or bromine atoms.

$R^{27}$ particularly preferably represents methyl, ethyl, trifluoromethyl, difluoromethyl, difluorochloromethyl or trichloromethyl.

$R^{27}$ very particularly preferably represents methyl, trifluoromethyl, difluoromethyl or Trichloromethyl.

$R^{28}$ and $R^{29}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{28}$ and $R^{29}$ independently of one another particularly preferably represent hydrogen, fluorine, chlorine, bromine, methyl, ethyl, trifluoromethyl, difluoromethyl, difluorochloromethyl or trichloromethyl.

$R^{28}$ and $R^{29}$ independently of one another very particularly preferably represent hydrogen, fluorine, chlorine, bromine, methyl, trifluoromethyl, difluoromethyl or trichloromethyl.

$R^{28}$ and $R^{29}$ especially preferably each represent hydrogen.

$R^{30}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{30}$ particularly preferably represents hydrogen, fluorine, chlorine, bromine, iodine, methyl, ethyl, trifluoromethyl, difluoromethyl, difluorochloromethyl or trichloromethyl.

$R^{30}$ very particularly preferably represents hydrogen, fluorine, chlorine, bromine, methyl, trifluoromethyl, difluoromethyl or trichloromethyl.

$R^{30}$ especially preferably represents methyl.

$R^{31}$ and $R^{32}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{31}$ and $R^{32}$ independently of one another particularly preferably represent hydrogen, fluorine, chlorine, bromine, nitro, methyl, ethyl, trifluoromethyl, difluoromethyl, difluorochloromethyl or trichloromethyl.

$R^{31}$ and $R^{32}$ independently of one another very particularly preferably represent hydrogen, fluorine, chlorine, bromine, methyl, trifluoromethyl, difluoromethyl or trichloromethyl.

$R^{31}$ and $R^{32}$ especially preferably each represent hydrogen.

$R^{33}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{33}$ particularly preferably represents hydrogen, fluorine, chlorine, bromine, iodine, methyl, ethyl, trifluoromethyl, difluoromethyl, difluorochloromethyl or trichloromethyl.

$R^{33}$ very particularly preferably represents hydrogen, fluorine, chlorine, bromine, methyl, trifluoromethyl, difluoromethyl or trichloromethyl.

$R^{33}$ especially preferably represents methyl.

$R^{34}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{34}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{34}$ very particularly preferably represents hydrogen, fluorine, chlorine, bromine, amino, methylamino, dimethylamino, methyl, trifluoromethyl, difluoromethyl or trichloromethyl.

$R^{34}$ especially preferably represents amino, methylamino, dimethylamino, methyl or trifluoromethyl.

$R^{35}$ preferably represents fluorine, chlorine, bromine, methyl, ethyl or $C_1$-$C_2$-haloalkyl having 1 to 5 fluorine, chlorine and/or bromine atoms.

$R^{35}$ particularly preferably represents fluorine, chlorine, bromine, methyl, ethyl, trifluoromethyl, difluoromethyl, difluorochloromethyl or trichloromethyl.

$R^{35}$ very particularly preferably represents fluorine, chlorine, bromine, methyl, trifluoromethyl, difluoromethyl or trichloromethyl.

$R^{35}$ especially preferably represents methyl, trifluoromethyl or difluoromethyl.

$R^{36}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{36}$ very particularly preferably represents hydrogen, fluorine, chlorine, bromine, amino, methylamino, dimethylamino, methyl, trifluoromethyl, difluoromethyl or trichloromethyl.

$R^{36}$ especially preferably represents amino, methylamino, dimethylamino, methyl or trifluoromethyl.

$R^{37}$ preferably represents fluorine, chlorine, bromine, methyl, ethyl or $C_1$-$C_2$-haloalkyl having 1 to 5 fluorine, chlorine and/or bromine atoms.

$R^{37}$ particularly preferably represents fluorine, chlorine, bromine, methyl, ethyl, trifluoromethyl, difluoromethyl, difluorochloromethyl or trichloromethyl.

$R^{37}$ very particularly preferably represents fluorine, chlorine, bromine, methyl, trifluoromethyl, difluoromethyl or trichloromethyl.

$R^{37}$ especially preferably represents methyl, trifluoromethyl or difluoromethyl.

$R^{38}$ preferably represents fluorine, chlorine, bromine, methyl, ethyl or $C_1$-$C_2$-haloalkyl having 1 to 5 fluorine, chlorine and/or bromine atoms.

$R^{38}$ particularly preferably represents fluorine, chlorine, bromine, methyl, ethyl, trifluoromethyl, Difluoromethyl, difluorochloromethyl or trichloromethyl.

$R^{38}$ very particularly preferably represents fluorine, chlorine, bromine, methyl, trifluoromethyl, difluoromethyl or trichloromethyl.

$R^{39}$ preferably represents hydrogen, methyl or ethyl.

$R^{39}$ particularly preferably represents methyl.

$R^{40}$ preferably represents fluorine, chlorine, bromine, methyl or ethyl.

$R^{40}$ particularly preferably represents fluorine, chlorine or methyl.

$R^{41}$ preferably represents methyl, ethyl or $C_1$-$C_2$-haloalkyl having 1 to 5 fluorine, chlorine and/or bromine atoms.

$R^{41}$ particularly preferably represents methyl, ethyl, trifluoromethyl, difluoromethyl, difluorochloromethyl or trichloromethyl.

$R^{41}$ very particularly preferably represents methyl, trifluoromethyl, difluoromethyl or trichloromethyl.

$R^{41}$ especially preferably represents methyl or trifluoromethyl.

$R^{42}$ preferably represents hydrogen, fluorine, chlorine, bromine, methyl, ethyl or $C_1$-$C_2$-haloalkyl having 1 to 5 fluorine, chlorine and/or bromine atoms.

$R^{42}$ particularly preferably represents hydrogen, fluorine, chlorine, bromine, methyl or trifluoromethyl.

$R^{43}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{43}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{43}$ very particularly preferably represents fluorine, chlorine, bromine, iodine, methyl, trifluoromethyl, difluoromethyl or trichloromethyl.

$R^{44}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{44}$ particularly preferably represents hydrogen, methyl, ethyl, trifluoromethyl, methoxymethyl, ethoxymethyl, hydroxymethyl or hydroxyethyl.

$R^{44}$ very particularly preferably represents methyl or methoxymethyl.

$R^{45}$ preferably represents hydrogen, fluorine, chlorine, bromine, methyl, ethyl or $C_1$-$C_2$-haloalkyl having 1 to 5 fluorine, chlorine and/or bromine atoms.

$R^{45}$ particularly preferably represents hydrogen, fluorine, chlorine, bromine, methyl, ethyl, trifluoromethyl, difluoromethyl or trichloromethyl.

$R^{45}$ very particularly preferably represents hydrogen or methyl.

$R^{46}$ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

$R^{46}$ particularly preferably represents hydrogen, fluorine, chlorine, bromine, iodine, cyano, methyl, ethyl, isopropyl, trifluoromethyl, difluoromethyl, difluorochloromethyl or trichloromethyl.

$R^{46}$ very particularly preferably represents hydrogen, methyl, difluoromethyl or trifluoromethyl.

$R^{47}$ preferably represents hydrogen, fluorine, chlorine, bromine, methyl, ethyl or $C_1$-$C_2$-haloalkyl having 1 to 5 fluorine, chlorine and/or bromine atoms.

$R^{47}$ particularly preferably represents hydrogen, fluorine, chlorine, bromine, iodine, methyl or trifluoromethyl.

$R^{47}$ very particularly preferably represents hydrogen.

$R^{48}$ preferably represents methyl, ethyl, n-propyl or isopropyl.

$R^{48}$ particularly preferably represents methyl or ethyl.

Preference is given to those compounds of the formula (I) in which all radicals each have the meanings mentioned above as being preferred.

Particular preference is given to those compounds of the formula (I) in which all radicals each have the meanings mentioned above as being particularly preferred.

Very particular preference is given to those compounds of the formula (I) in which all radicals each have the meanings mentioned above as being very particularly preferred.

Preferred, and in each case to be understood as a sub-group of tire compounds of the formula (I) mentioned above, are the following groups of novel carboxamides:

Group 1: 2-alkylcycloalk(en)ylcarboxamides of the formula (I-g)

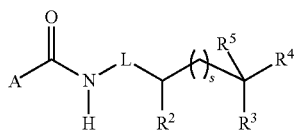

in which s, L, $R^2$, $R^3$, $R^4$, $R^5$ and A are as defined above.

Group 2: 2-alkylcycloalk(en)ylcarboxamides of the formula (I-b)

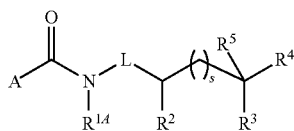

in which s, $R^{1A}$, L, $R^2$, $R^3$, $R^4$, $R^5$ and A are as defined above.

$R^{1A}$ preferably represents $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^6$, —CONR$^7$R$^8$ or —CH$_2$NR$^9$R$^{10}$.

$R^{1A}$ particularly preferably represents methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_3$)$_2$CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^6$, —CONR$^7$R$^8$ or —CH$_2$NR$^9$R$^{10}$.

$R^{1A}$ very particularly preferably represents methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Group 3: 2-alkylcycloalk(en)ylcarboxamides of the formula (I-c)

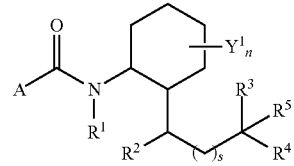

in which s, $R^1$, $R^2$, $R^3$, $R^4$, $R^5$, A, $Y^1$ and n are as defined above.

Emphasis is given to compounds of the formula (I-c), in which n represents 0.

Emphasis is given to compounds of the formula (I-c), in which $R^1$ represents hydrogen.

Emphasis is given to compounds of the formula (I-c), in which s represents 1.

Group 4: 2-alkylcycloalk(en)ylcarboxamides of the formula (I-d)

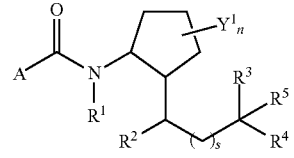

in which s, $R^1$, $R^2$, $R^3$, $R^4$, $R^5$, A, $Y^1$ and n are as defined above.

Emphasis is given to compounds of the formula (I-d), in which n represents 0.

Emphasis is given to compounds of the formula (I-d), in which $R^1$ represents hydrogen.

Emphasis is given to compounds of the formula (I-d), in which s represents 1.

Group 5: 2-alkylcycloalk(en)ylcarboxamides of the formula (I-e)

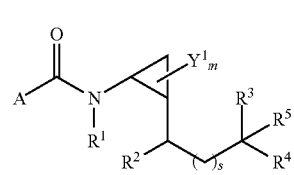

in which s, $R^1$, $R^2$, $R^3$, $R^4$, $R^5$, A, $Y^1$ and m are as defined above.

Emphasis is given to compounds of the formula (I-e), in which m represents 0.

Emphasis is given to compounds of the formula (I-e), in which $R^1$ represents hydrogen.

Emphasis is given to compounds of the formula (I-e), in which s represents 1.

Group 6: 2-alkylcycloalk(en)ylcarboxamides of the formula (I-f)

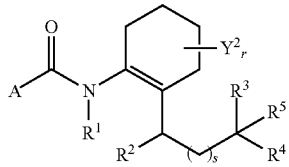
(I-f)

in which s, $R^1$, $R^2$, $R^3$, $R^4$, $R^5$, A, $Y^2$ and r are as defined above.

Emphasis is given to compounds of the formula (I-f), in which r represents 0.

Emphasis is given to compounds of the formula (I-f), in which $R^1$ represents hydrogen.

Emphasis is given to compounds of the formula (I-f), in which s represents 1.

Group 7: 2-alkylcycloalk(en)ylcarboxamides of the formula (I-h)

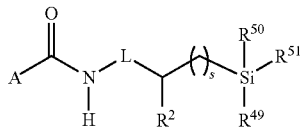
(I-h)

in which s, L, $R^2$, $R^{49}$, $R^{50}$, $R^{51}$ and A are as defined above.

Group 8: 2-alkylcycloalk(en)ylcarboxamides of the formula (I-i)

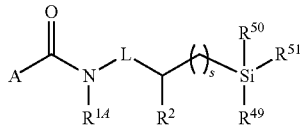
(I-i)

in which s, $R^{14}$, L, $R^2$, $R^{49}$, $R^{50}$, $R^{51}$ and A are as defined above.

Group 9: 2-alkylcycloalk(en)ylcarboxamides of the formula (I-k)

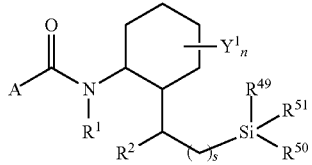
(I-k)

in which s, $R^1$, $R^2$, $R^{49}$, $R^{50}$, $R^{51}$, A, $Y^1$ and n are as defined above.

Emphasis is given to compounds of the formula (I-k), in which n represents 0.

Emphasis is given to compounds of the formula (I-k), in winch $R^1$ represents hydrogen.

Emphasis is given to compounds of the formula (I-k), in which s represents 1.

Group 10: 2-alkylcycloalk(en)ylcarboxamides of the formula (I-l)

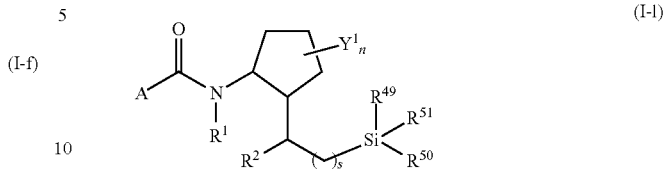
(I-l)

in which s, $R^1$, $R^2$, $R^{49}$, $R^{50}$, $R^{51}$, A, $Y^1$ and n are as defined above.

Emphasis is given to compounds of the formula (I-l), in which n represents 0.

Emphasis is given to compounds of the formula (I-l), in which $R^1$ represents hydrogen.

Emphasis is given to compounds of the formula (I-l), in which s represents 1.

Group 11: 2-alkylcycloalk(en)ylcarboxamides of the formula (I-m)

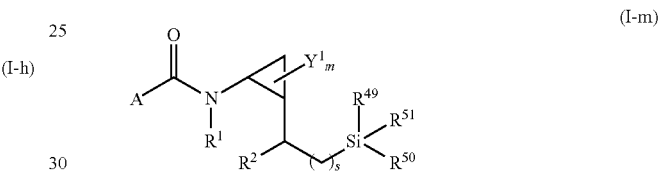
(I-m)

in which s, $R^1$, $R^2$, $R^{49}$, $R^{50}$, $R^{51}$, A, $Y^1$ and m are as defined above.

Emphasis is given to compounds of the formula (I-m), in which m represents 0.

Emphasis is given to compounds of the formula (I-m), in which $R^1$ represents hydrogen.

Emphasis is given to compounds of the formula (I-m), in which s represents 1.

Group 12: 2-alkylcycloalk(en)ylcarboxamides of the formula (I-n)

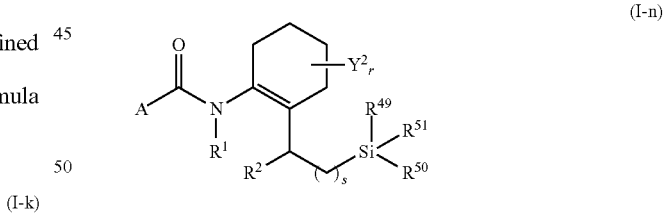
(I-n)

in which s, $R^1$, $R^2$, $R^{49}$, $R^{50}$, $R^{51}$, A, $Y^2$ and r are as defined above.

Emphasis is given to compounds of the formula (I-n), in which r represents 0.

Emphasis is given to compounds of the formula (I-n), in which $R^1$ represents hydrogen.

Emphasis is given to compounds of the formula (I-n), in which s represents 1.

Emphasis is given to compounds of the formula (I) (and also of groups 2 to 6 and 8 to 12), in which $R^1$ or $R^{14}$ represents formyl.

Emphasis is furthermore given to compounds of the formula (I) (and also of groups 2 to 6 and 8 to 12), in which $R^1$ or $R^{14}$ represents —C(=O)C(=O)$R^6$, where $R^6$ is as defined above.

Saturated or unsaturated hydrocarbon radicals, such as alkyl or alkenyl, may in each case be straight-chain or branched as far as this is possible, including in combination with heteroatoms, such as, for example, in alkoxy.

Optionally substituted radicals may be mono- or polysubstituted, where in the case of polysubstitution the substituents may be identical or different. Thus, the definition dialkylamino also embraces an amino group which is substituted asymmetrically by alkyl, such as, for example, methylethylamino.

Halogen-substituted radicals, such as, for example, haloalkyl, are mono- or polyhalogenated. In the case of polyhalogenation, the halogen atoms may be identical or different. Here, halogen represents fluorine, chlorine, bromine and iodine, in particular fluorine, chlorine and bromine.

The general or preferred radical definitions or illustrations given above can be combined as desired between the respective ranges and preferred ranges. They apply both to the end products and, correspondingly, to precursors and intermediates. In particular, the compounds mentioned in groups 1 to 6 may be combined both with the general and with the preferred, particularly preferred, etc., meanings, here, too, any combinations between the preferred ranges being possible.

DESCRIPTION OF THE PROCESSES ACCORDING TO THE INVENTION FOR PREPARING THE 2-alkylcycloalk(en)ylcarboxamides OF THE FORMULA (I) AND THE INTERMEDIATES Process (a)

Using 5-fluoro-1,3-dimethyl-1H-pyrazole-4-carbonyl chloride and 2-(1,3-dimethylbutyl)-cyclohexanamine as starting material, the process (a) according to the invention can be illustrated by the formula scheme below:

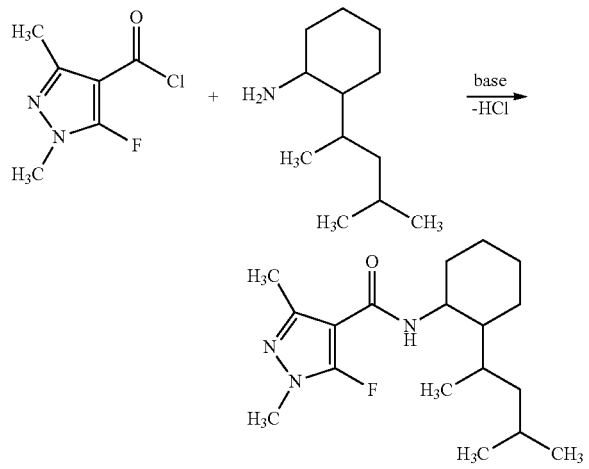

The formula (II) provides a general definition of the carboxylic acid derivatives required as starting materials for carrying out the process (a) according to the invention. In this formula (II), A preferably, particularly preferably or very particularly preferably has those meanings which have already been mentioned in connection with the description of the compounds of the formula (I) according to the invention as being preferred, particularly preferred and very particularly preferred, respectively, for this radical. $X^1$ preferably represents chlorine, bromine or hydroxyl.

The carboxylic acid derivatives of the formula (II) are known and/or can be prepared by known processes (cf. WO 03/066609, WO 03/066610, EP-A 0 545 099, EP-A 0 589 301, EP-A 0 589 313 and U.S. Pat. No. 3,547,917).

The formula (III) provides a general definition of the aniline derivatives furthermore required as starting materials for carrying out the process (a) according to the invention. In this formula (III), X, s, $R^1$, L and $R^2$ preferably, particularly preferably or very particularly preferably have those meanings which have already been mentioned in connection with the description of the compounds of the formula (I) according to the invention as being preferred, particularly preferred and very particularly preferred, respectively, for these radicals or this index.

Some of the aniline derivatives of the formula (III) are already known, or they can be obtained by known processes (cf, for example, EP-A 0 589 313).

It is also possible to prepare initially aniline derivatives of the formula (III-a)

in which X, s, L and $R^2$ are as defined above and to react these, if appropriate, subsequently with halides of the formula (IV)

$$R^{1A}-X^2 \tag{IV}$$

in which $R^{3A}$ and $X^4$ are as defined above, in the presence of a base and in the presence of a diluent. [The reaction conditions of the process (b) according to the invention apply correspondingly.]

Aniline derivatives of the formula (III) are also obtained when (c) cyclic ketones of the formula (V)

in which $L^{1a}$ represents $C_2$-$C_6$-alkylene ($C_2$-$C_6$-alkanediyl) which is optionally mono- to tetra-substituted by identical or different substituents from the group consisting of fluorine, chlorine, $C_1$-$C_4$-alkyl or $C_1$-$C_4$-haloalkyl, are initially reacted with carbonyl compounds of the formula (VI)

in which X, s and $R^2$ are as defined above, in the presence of a base to give the compounds of the formulae (VIIa) and (VIIb)

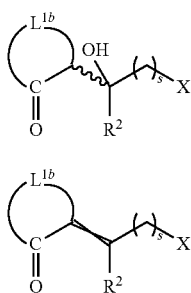

(VIIa)

(VIIb)

in which

X, S and $R^2$ are as defined above and $L^{1b}$ represents $C_1$-$C_5$-alkylene ($C_1$-$C_5$-alkanediyl) which is optionally mono- to tetra-substituted by identical or different substituents from the group consisting of fluorine, chlorine, $C_1$-$C_4$-alkyl and $C_1$-$C_4$-haloalkyl, and these are then subjected to a reductive amination by customary methods.

The formula (V) provides a general definition of the cyclic ketones required as starting materials for carrying out the process (c) according to the invention. In this formula (V), $L^{1a}$ preferably represents —(CH$_2$)$_2$— which is optionally substituted m times by $Y^1$ or represents —(CH$_2$)$_3$—, —(CH$_2$)$_4$—, —(CH$_2$)$_5$— or —(CH$_2$)$_6$—, each of which is optionally substituted n times by $Y^1$, where m, n and $Y^1$ are as defined above. $L^{1a}$ particularly preferably represents —(CH$_2$)$_2$— which is optionally substituted m times by $Y^1$ or represents —(CH$_2$)$_4$— or —(CH$_2$)$_5$— which are each optionally substituted n times by $Y^1$, where m, n and $Y^1$ are as defined above.

The formula (VI) provides a general definition of the carbonyl compounds furthermore required as starting materials for carrying out the process (c) according to the invention. In this formula (VI), X, s and $R^2$ preferably, particularly preferably and very particularly preferably have those meanings which have already been mentioned in connection with the description of the compounds of the formula (I) according to the invention as being preferred, particularly preferred and very particularly preferred, respectively, for these radicals.

The formulae (VIIa) and (VIIb) provide general definitions of the compounds formed as intermediates when carrying out the process (c) according to the invention. In these formulae (VIIa) and (VIIb) $L^{1b}$ preferably represents —(CH$_2$)— which is optionally substituted m times by $Y^1$ or represents —(CH$_2$)$_2$—, —(CH$_2$)$_3$—, —(CH$_2$)$_4$— or —(CH$_2$)$_5$—, each of which is optionally substituted n times by $Y^1$, where m, n and $Y^1$ are as defined above. $L^{1b}$ particularly preferably represents —(CH$_2$)— which is optionally substituted m times by $Y^1$ or represents —(CH$_2$)$_3$— or —(CH$_2$)$_4$—, each of which is optionally substituted n times by $Y^1$, where m, n and $Y^1$ are as defined above. X, s and $R^2$ preferably, particularly preferably or very particularly preferably have those meanings which have already been mentioned in connection with the description of the compounds of the formula (I) according to the invention as being preferred, particularly preferred and very particularly preferred, respectively, for these radicals.

Cyclic ketones of the formula (V) and carbonyl compounds of the formula (VI) are known or can be prepared by processes known from the literature (Organic Letters 2001, Vol. 3, 573; Tetrahedron Letters 42 (2001) 4257).

Process (b)

Using N-[2-(1,3-dimethylbutyl)cyclohexyl]-5-fluoro-1,3-dimethyl-1H-pyrazole-4-carboxamide and acetyl chloride as starting materials, the course of the process (b) according to the invention can be illustrated by the formula scheme below:

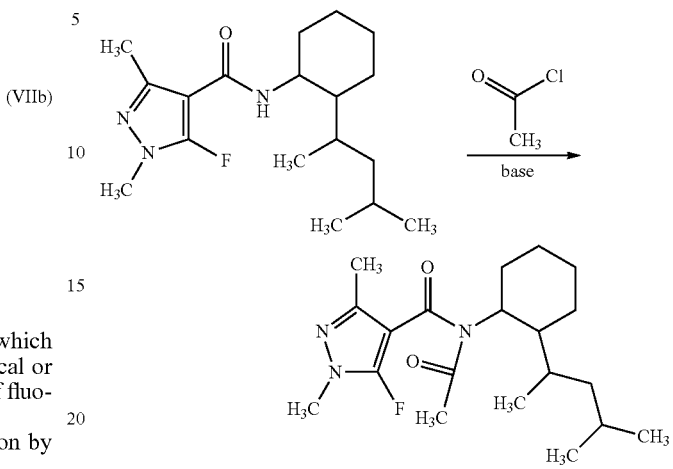

The formula (I-a) provides a general definition of the 2-alkylcycloalk(en)ylcarboxamides required as starting materials for carrying out the process (b) according to the invention. In this formula (I-a), X, s, L, $R^2$ and A preferably, particularly preferably or very particularly preferably have those meanings which have already been mentioned in connection with the description of the compounds of the formula (I) according to the invention as being preferred, particularly preferred and very particularly preferred, respectively, for these radicals.

The compounds of the formula (I-a) are compounds according to the invention and can be prepared by process (a).

The formula (IV) provides a general definition of the halides furthermore required as starting materials for carrying out the process (b) according to the invention. In this formula (IV), $R^{1A}$ preferably, particularly preferably or very particularly preferably has those meanings which have already been mentioned above for the compounds of the formula (I-b) as being preferred, particularly preferred and very particularly preferred, respectively, for this radical. $X^4$ represents chlorine, bromine or iodine.

Halides of the formula (IV) are known.

Reaction Conditions

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl iso-butyl ketone or cyclohexanone; nitriles, such as acetonitrile, propionitrile, n- or isobutyronitrile or benzonitrile; amides, such as N,N-dimethylformamide, N,N-dimetylacetamide, N-methylformanilide, N-methylpyrrolidone or hexamethylphosphoric triamide; mixtures thereof with water or pure water.

The process (a) according to the invention is, if appropriate, carried out in the presence of a suitable acid acceptor.

Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (a) according to the invention is, if appropriate, carried out in the presence of a suitable condensing agent. Suitable condensing agents are all condensing agents usually used for such amidation reactions. By way of example, mention may be made of acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate.

The process (a) according to the invention is, if appropriate, carried out in the presence of a catalyst. By way of example, mention may be made of 4-dimethylaminopyridine, 1-hydroxybenzotriazole or dimethylformamide.

When carrying out the process (a) according to the invention, the reaction temperatures can be varied within a relatively wide range. In general, the process is carried out at temperatures of from 0° C. to 150° C., preferably at temperatures from 0° C. to 80° C.

For carrying out the process (a) according to the invention for preparing the compounds of the formula (I), in general from 0.8 to 15 mol, preferably from 0.8 to 8 mol, of aniline derivative of the formula (III) are employed per mole of the carboxylic acid derivative of the formula (II).

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (b) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (b) according to the invention, the reaction temperatures can be varied within a relatively large range. In general, the process is carried out at temperatures of from 0° C. to 150° C., preferably at temperatures of from 20° C. to 110° C.

For carrying out the process (b) according to the invention for preparing the compounds of the formula (I), in general from 0.2 to 5 mol, preferably from 0.5 to 2 mol, of halide of the formula (IV) are employed per mole of the 2-alkylcycloalk(en)ylcarboxamide of the formula (I-a).

Unless indicated otherwise, all processes according to the invention are generally carried out under atmospheric pressure. However, it is also possible to operate under elevated or reduced pressure—in general between 0.1 bar and 10 bar.

Suitable diluents for carrying out the process (c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide, alcohols, such as, for example, methanol, ethanol, isopropanol, n-, sec- or tert-butanol, mixtures thereof with water or pure water.

The process (c) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (c) according to the invention, the reaction temperatures may be varied within a relatively wide range. In general, the process is carried out at temperatures from −20° C. to 150° C., preferably at temperatures of from 0° C. to 110° C.

For carrying out the process (c) according to the invention for preparing the compounds of the formula (III), in general from 0.2 to 5 mol, preferably from 0.5 to 2 mol, of carbonyl compound of the formula (VI) are employed per mole of the cyclic ketone of the formula (V).

Unless indicated otherwise, all processes according to the invention are generally carried out under atmospheric pressure. However, it is also possible to operate under elevated or reduced pressure—in general between 0.1 bar and 10 bar.

Process c-2 Reductive Amination

Suitable diluents for carrying out the process (c-2) according to the invention are all inert organic solvents. These preferably include aliphatic, alicyclic or aromatic hydrocarbons, such as, for example, petroleum ether, hexane, heptane, cyclohexane, methylcyclohexaue, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide, alcohols, such as, for example, methanol, ethanol, isopropanol, n-, sec-, or tert-butanol, mixtures thereof with water or pure water.

The reductive amination in the process (c) according to the invention is carried out in the presence of an amine and a reducing agent. Suitable amine components are ammonia, ammonia salts, such as, for example, ammonium formate, but also monosubstituted ammonia, such as, for example, methylamine, ethylamine, propylamine, cyclopropylamine, etc. Suitable reducing agents are all customary inorganic or organic reducing agents. These preferably include alkaline earth metal or alkali metal hydrides, or borohydrides, such as, for example, sodium hydride, sodium cyanoborohydride, sodium borohydride, or sources of hydrogen, such as, for example, elemental hydrogen, hydrazine, cyclohexanediene or formates, or else the formates of the corresponding amine components.

The reductive amination in the process (c) according to the invention is, if appropriate, carried out in the presence of a catalyst. Suitable catalysts are commercial catalysts, such as, for example, hydrogenation catalysts, for example elemental Pd, Ni (or else Raney nickel), Pt, Fe, Ru, Os or salts thereof. These catalysts may be supported on carriers, such as, for example, carbon, silica, zeolites, etc., or be stabilized by ligands.

When carrying out the reductive amination in the process (c) according to the invention, the reaction temperatures may be varied within a relatively wide range. In general, the process is carried out at temperatures from 0° C. to 150° C., preferably at temperatures of from 20° C. to 110° C.

For the reductive amination in the process (c) according to the invention for preparing the compounds of the formula (III), in general from 0.2 to 50 mol, preferably from 1 to 20 mol, of amine and reducing agent, and also 0.01-10 mol % of catalyst are employed per mole of the cyclic ketone of the formula (V).

Unless indicated otherwise, all processes according to the invention are generally carried out under atmospheric pressure. However, it is also possible to carry out the processes under elevated or reduced pressure, in general between 0.1 bar and 10 bar.

The substances according to the invention exhibit a potent microbicidal activity and can be employed in plant protection and in the protection of materials for controlling undesirable microorganisms such as fungi and bacteria.

Fungicides can be employed in plant protection for controlling Plasmodiophoromycetes, Oomycetes, Chytridiomycetes, Zygomycetes, Ascomycetes, Basidiomycetes and Deuteromycetes.

Bactericides cat be employed in plant protection for combating Pseudomonadaceae, Rhizobiaceae, Enterobacteriaceae, Corynebacteriaceae and Streptomycetaceae.

Examples which may be mentioned, but not by limitation, of some pathogens of fungal and bacterial diseases which come under the abovementioned general terms are:

Diseases caused by powdery mildew pathogens, such as, for example

Blumeria species such as, for example, Blumeria graminis;
Podosphaera species such as, for example, Podosphaera leucotricha;
Sphaerotheca species such as, for example, Sphaerotheca fuliginea;
Uncinula species such as, for example, Uncinula necator;
diseases caused by rust pathogens such as, for example,
Gymnosporangium species such as, for example, Gymnosporangium sabinae
Hemileia species such as, for example, Hemileia vastatrix;
Phakopsora species such as, for example, Phakopsora pachyrhizi and Phakopsora meibomiae:
Puccinia species such as, for example, Puccinia recondita;
Uromyces species such as, for example, Uromyces appendiculatus;
diseases caused by pathogens from the Oomycetene group such as, for example,
Bremia species such as, for example, Bremia lactucae;
Peronospora species such as, for example, Peronospora pisi or P. brassicae;
Phytophthora species such as, for example, Phytophthora infestans;
Plasmopara species such as, for example, Plasmopara viticola;
Pseudoperonospora species such as, for example, Pseudoperonospora humuli or Pseudoperonospora cubensis;
Pythium species such as, for example, Pythium ultimum;
leaf spot diseases and leaf wilts caused by, for example,
Alternaria species such as, for example, Alternaria solani;
Cercospora species such as, for example, Cercospora beticola;
Cladiosporum species such as, for example, Cladiosporium cucumerinum;
Cochliobolus species such as, for example, Cochliobolus sativus (conidial form: Drechslera, syn: Helminthosporium);
Colletotrichum species such as, for example, Colletotrichum lindemuthanium;
Cycloconium species such as, for example, Cycloconium oleaginum;
Diaporthe species such as, for example, Diaporthe citri;
Elsinoe species such as, for example, Elsinoe fawcettii;
Gloeosporium species such as, for example, Gloeosporium lacticolor;
Glomerella species such as, for example, Glomerella cingulata;
Guignardia species such as, for example, Guignardia bidwelli;
Leptosphaeria species such as, for example, Leptosphaeria maculans;
Magnaporthe species such as, for example, Magnaporthe grisea;
Mycosphaerella species such as, for example, Mycosphaerelle graminicola;
Phaeosphaeria species such as, for example, Phaeosphaeria nodorum;
Pyrenophora species such as, for example, Pyrenophora teres;
Ramularia species such as, for example, Ramularia collocygni;
Rhynchosporium species such as, for example, Rhynchosporium secalis;

*Septoria* species such as, for example, *Septoria apii;*
*Typhula* species such as, for example, *Typhula incarnata;*
*Venturia* species such as, for example, *Venturia inaequalis;*
root and stem diseases caused by, for example,
*Corticium* species such as, for example, *Corticium graminearum;*
*Fusarium* species such as, for example, *Fusarium oxysporum;*
*Gaeumannomyces* species such as, for example, *Gaeumannomyces graminis;*
*Rhizoctonia* species such as, for example, *Rhizoctonia solani;*
*Tapesia* species such as, for example, *Tapesia acuformis;*
*Thielaviopsis* species such as, for example, *Thielaviopsis basicola;*
car and panicle diseases (including maize cobs), caused by, for example,
*Alternaria* species such as, for example, *Alternaria* spp.;
*Aspergillus* species such as, for example, *Aspergillus flavus;*
*Cladosporium* species such as, for example, *Cladosporium* spp.;
*Claviceps* species such as, for example, *Claviceps purpurea;*
*Fusarium* species such as, for example, *Fusarium culmorum;*
*Gibberella* species such as, for example, *Gibberella zeae;*
*Monographella* species such as, for example, *Monographella nivalis;*
diseases caused by smuts such as, for example,
*Sphacelotheca* species such as, for example, *Sphacelotheca reiliana;*
*Tilletia* species such as, for example, *Tilletia caries;*
*Urocystis* species such as, for example, *Urocystis occulta;*
*Ustilago* species such as, for example, *Ustilago nuda;*
fruit rots caused by, for example,
*Aspergillus* species such as, for example, *Aspergillus flavus;*
*Botrytis* species such as, for example, *Botrytis cinerea;*
*Penicillium* species such as, for example, *Penicillium expansum;*
*Sclerotinia* species such as, for example, *Sclerotinia sclerotiorum;*
*Verticilium* species such as, for example, *Verticilium alboatrum;*
seed- and soil-borne rot and wilts, and seedling diseases, caused by, for example,
*Fusarium* species such as, for example, *Fusarium culmorum,*
*Phytophthora* species such as, for example, *Phytophthora cactorum;*
*Pythium* species such as, for example, *Pythium ultimum;*
*Rhizoctonia* species such as, for example, *Rhizoctonia solani;*
*Sclerotium* species such as, for example, *Sclerotium rolfsii;*
cankers, galls and witches' broom disease, caused by, for example,
*Nectria* species such as, for example, *Nectria galligena;*
Wilts caused by, for example,
*Monilinia* species such as, for example, *Monilinia laxa;*
deformations of leaves, flowers and fruits, caused by, for example,
*Taphrina* species such as, for example, *Taphrina deformans;*
degenerative diseases of woody species, caused by, for example,
*Esca* species such as, for example, *Phaemoniella clamydospora;*
diseases of inflorescences and seeds, caused by, for example,
*Botrytis* species such as, for example, *Botrytis cinerea;*
diseases of the plant tubers, caused by, for example,
*Rhizoctonia* species such as, for example, *Rhizoctonia solani;*
diseases caused by bacterial pathogens such as, for example,
*Xanthomonas* species such as, for example, *Xanthomonas campestris* pv. oryzae;
*Pseudomonas* species such as, for example, *Pseudomonas syringae* pv. lachrymans;
*Erwinia* species such as, for example, *Erwinia amylovora.*

The following diseases of soybeans can preferably be controlled:
Fungal diseases on leaves, stems, pods and seeds caused by, for example,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);
fungal diseases on roots and the stem base caused by, for example,
black root rot (*Calonectria crotalariae*), charcoal rot (*Macrophomina phaseolina*), fosarium blight or wilt, root rot, and pod and collar rot (*Fusariurn oxysporum, Fusarium orthoccras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defences against attack by undesired microorganisms.

Plant-strengthening (resistance-inducing) substances are understood as meaning, in the present context, those substances which are capable of stimulating the defence system of plants in such a way that, when subsequently inoculated with undesired microorganisms, the heated plants display a substantial degree of resistance to these microorganisms.

In the present case, undesired microorganisms are understood as meaning phytopathogenic fungi, bacteria and viruses. Thus, the substances according to the invention can be employed for protecting plants against attack by the above-mentioned pathogens within a certain period of time after the treatment. The period of time within which their protection is effected is generally extended from 1 to 10 days, preferably 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example against *Botrytis*, *Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean parts and organs of the plants, such as shoot, leaf, flower and root, examples which may be mentioned being leaves, needles, stalks, steins, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the substances according to the invention can be employed for protecting industrial materials against attack and destruction by undesired microorganisms.

In the present context, industrial materials are understood as meaning non live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:

*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example, to improve the activity spectrum or prevent the development of resistance. In many instances, synergistic effects are obtained, i.e. the activity of the mixture exceeds the activity of the individual components.

Examples of co-components in mixtures are the following compounds:

Fungicides:
1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;
2) mitosis and cell division inhibitors: for example benomyl, carbendazim, diethofencarb, ethaboxam, fuberidazole, pencycuron, thiabendazole, thiophanate-methyl, zoxamide;
3) respiration inhibitors (inhibitors of the respiratory chain):
3.1) inhibitors which act on complex I of the respiratory chain: for example diflumetorim;
3.2) inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;
3.3) inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;
4) decouplers: for example dinocap, fluazinam, meptyldinocap;
5) ATP production inhibitors: for example fentin acetate, fentin chloride, fentin hydroxide, silthiofam;
6) amino acid and protein biosynthesis inhibitors: for example andoprim, blasticidin-S, cyprodinil, kasugamycin, kasugamycin hydrochloride hydrate, mepanipyrim, pyrimethanil;
7) signal transduction inhibitors: for example fenpiclonil, fludioxonil, quinoxyfen;
8) lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;
9) inhibitors of ergosterol biosynthesis: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;
10) cell wall synthesis inhibitors: for example benthiavalicarb, dimethomorph, flumorph, iprovalicarb, polyoxins, polyoxorim, validamycin A;
11) melanin biosynthesis inhibitors: for example carpropamid, diclocymet, fenoxanil, phthalide, pyroquilon, tricyclazole;
12) resistance inductors: for example acibenzolar-S-methyl, probenazole, tiadinil;
13) compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;
14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamid, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino) acetamide, 1-(4-chlorophenyl)-2-(1H-1,2,4-triazol-1-yl) cycloheptanol, 1-[(4-methoxyphenoxy)methyl]-2,2-dimethylpropyl-1H-imidazole-1-carboxylate, 2-(4-chlorophenyl)-N-{2-[3-methoxy-4-(prop-2-yn-1-yloxy) phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloropyridine-2,6-dicarbonitrile, 3,4-dichloro-N-(2-cyanophenyl) isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4] triazolo-[1,5-a]pyrimidine-7-amine, 5-chloro-7-(4-methylpiperidin-1-yl)-6-(2,4,6-trifluoropheny)[1,2,4] triazolo-[1,5-a]pyrimidine, 5-chloro-N-[(1R)-1,2-dimethylpropyl]-6-(2,4,6-trifluorophenyl)[1,2,4]triazolo [1,5-a]-pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl) methoxy]ethanimido-yl}benzyl)carbamate, methyl (2E)-2-{2-[({cyclopropyl[(4-methoxyphenyl)imino] methyl}thio)methyl]-phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxy-benzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-$N^2$-(methylsulphonyl)valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl]ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl} 1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid, Bactericides:

Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
1. Acetylcholine esterase (AChE) inhibitors
    1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
    1.2 Organophosphates (for example acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)
2. Sodium channel modulators/voltage-dependent sodium channel blockers
    2.1 Pyrethroids (for example acrinathrin, allethrin (d-cis-trans, d-trans), beta-cyfluthrin, bifenthrin, bioallethrin, bioallethrin-S-cyclopentyl isomer, bioethanomethrin, biopermethrin, biopermethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R transisomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))
    2.2 Oxadiazines (for example indoxacarb)
3. Acetylcholine receptor agonists/antagonists
    3.1 Chloronicotinyls/neonicotinoids (for example acetamiprid, clothianidin, dinotefuran, imidacloprid, nitenpyram, nithiazine, thiacloprid, thiamethoxam)
    3.2 Nicotine, bensultap, cartap
4. Acetylquoline receptor modulators
    4.1 Spinosyns (for example spinosad)
5. GABA-controlled chloride channel antagonists
    5.1 Cyclodiene organochlorines (for example camphechlor, chlordane, endosulfan, gamma-HCH, HCH, heptachlor, lindane, methoxychlor
    5.2 Fiprols (for example acetoprole, ethiprole, fipronil, vaniliprole)
6. Chloride channel activators
    6.1 Mectins (for example abamectin, avermectin, emamectin, emamectin benzoate, ivermectin, milbemectin, milbemycin)
7. Juvenile hormone mimetics
    (for example diofenolan, epofenonane, fenoxycarb, hydroprene, kinoprene, methoprene, pyriproxifen, triprene)
8. Ecdysone agonists/disruptors
    8.1 Diacylhydrazines (for example chromafenozide, halofenozide, methoxyfenozide, tebufenozide)
9. Chitin biosynthesis inhibitors
    9.1 Benzoylureas (for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron)
    9.2 Buprofezin
    9.3 Cyromazine
10. Inhibitors of oxidative phosphorylation, ATP disrupters
    10.1 Diafenthiuron
    10.2 Organotins (for example azocyclotin, cyhexatin, fenbutatin oxide)
11. Uncouplers of oxidative phosphorylation by interrupting the H-proton gradient
    11.1 Pyrroles (for example chlorfenapyr)
    11.2 Dinitrophenols (for example binapacyrl, dinobuton, dinocap, DNOC)
12. Site-I electron transport inhibitors
    12.1 METIs (for example fenazaquin, fenpyroximate, pyrimidifen, pyridaben, tebufenpyrad, tolfenpyrad)
    12.2 Hydramethylnon
    12.3 Dicofol
13. Site-II electron transport inhibitors
    13.1 Rotenone
14. Site-III electron transport inhibitors
    14.1 Acequinocyl, fluacrypyrim
15. Microbial disrupters of the insect gut membrane
    *Bacillus thuringiensis* strains
16. Fat synthesis inhibitors
    16.1 Tetronic acids (for example spirodiclofen, spiromesifen)
    16.2 Tetramic acids (for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro-[4.5]dec-3-en-4-yl ethyl ester, CAS Reg. No.: 382608-10-8) and carbonic acid, cis-3-(2,5-dimethyl-phenyl)-8-methoxy-2-oxo-1-azaspiro[4.5]dec-3-en-4-yl ethyl ester (CAS Reg.-No.: 203313-25-1)]
17. Carboxamides
    (for example flonicamid)
18. Octopaminergic agonists
    (for example amitraz)
19. Inhibitors of magnesium-stimulated ATPase (for example propargite)
20. Phthalamides
    (for example $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg.-No.: 272451-65-7), flubendiamide)
21. Nereistoxin analogues
    (for example thiocyclam hydrogen oxalate, thiosultap sodium)
22. Biologicals, hormones or pheromones
    (for example azadirachtin, *Bacillus* spec., *Beauveria* spec., codlemone, *Metarhizium* spec., *Paecilomyces* spec., thuringiensin, *Verticillium* spec.)
23. Active compounds with unknown or unspecific mechanisms of action
    23.1 Fumigants (for example aluminium phosphide, methyl bromide, sulfuryl fluoride)
    23.2 Selective antifeedants (for example cryolite, flonicamid, pymetrozine)
    23.3 Mite growth inhibitors (for example clofentezine, etoxazole, hexythiazox)
    23.4 Amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methyl-phenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The enumeration of these fungi is no restriction whatsoever of the mycotic spectrum which can be controlled and is provided by illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plant can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, breeds, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, more developed root system, higher resistance of the plant variety or plant cultivar, increased growth of shoots, higher plant vitality, increased tolerance to high or low temperatures, increased tolerance to drought or to water or soil salinity, increased flowering performance, easier harvesting, accelerated maturation, higher harvest yields, larger fruit, increased plant size, greener leaf colour, earlier blossoming, better quality and/or a higher nutritional value of the harvested products, higher sugar concentration in the fruits, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defence of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulfonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya bean), Liberty Link® (tolerance to phosphinothricin, for example oilseed rape), IMI® (tolerance to imidazolinoses) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

Preparation of 2-(1,3-dimethylbutyl)cyclohexanamine

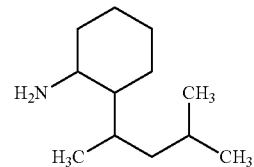

5 g of Ru/C (5%) are added to a solution comprising 20.0 g (0.113 mol) of 2-(1,3-dimethylbutyl)aniline in 300 ml of tetrahydrofuran, and the mixture is hydrogenated with 100 bar of hydrogen at 120° C. for 24 hours. After cooling to room temperature, the catalyst is filtered off through Celite 545 and the product is concentrated under reduced pressure. This gives 19.1 g (92.4% of theory) of 2-(1,3-dimethylbutyl)cyclohexanamine having a purity of 100% according to HPLC and a log P (pH 2.3) of 4.07.

Preparation of 4-(difluoromethyl)-N-[2-(1,3-dimethylbutyl)cyclohexyl]-2-methyl-1,3-thiazole-5-carboxamide

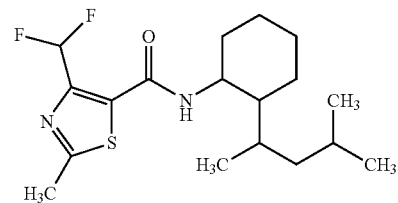 [SMILES: Cc1nc(C(F)F)c(C(=O)NC2CCCCC2C(C)CC(C)C)s1]

At room temperature, 0.104 g (0.82 mmol) of oxalyl chloride is added dropwise to a solution of 0.16 g (0.82 mmol) of 4-(difluoromethyl)-2-methyl-1,3-thiazole-5-carboxylic acid and a drop of DMF in 15 ml of dichloromethane, and the mixture is stirred at room temperature for 1 hour.

At room temperature, the acid chloride solution described above is added dropwise to a solution comprising 0.15 g (0.82 mmol) of 2-(1,3-dimethylbutyl)cyclohexanamine and 0.25 g (0.0025 mol) of triethylamine in 5 ml of dichloromethane, and the reaction mixture is stirred at room temperature for 12 hours.

The mixture is washed twice with in each case 10 ml of water, dried over sodium sulphate and concentrated under reduced pressure. The residue is chromatographed on silica gel using n-hexane/methyl tert-butyl ether (3:1). This gives 0.12 g (38.9% of theory) of 4-(difluoromethyl)-N-[2-(1,3-dimethylbutyl)cyclohexyl]-2-methyl-1,3-thiazole-5-carboxamide as a mixture of diastereomers having a content of 95% according to HPLC and a log P (pH 2.3) of 4.45/4.53.

TABLE 1

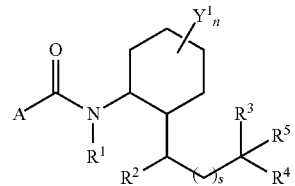

(I-c)

| No. | s | $R^1$ | $R^2$ | $R^3$ | $R^4$ | $R^5$ | A | logP*/ m.p. (°C.) |
|---|---|---|---|---|---|---|---|---|
| I-c-1 | 1 | H | $CH_3$ | $CH_3$ | $CH_3$ | H | 3-methyl-4-methyl-5-fluoro-1-methyl-pyrazole ($H_3C$, $CH_3$, F, N-$CH_3$) | 4.15 62-65° C. |
| I-c-2 | 1 | H | $CH_3$ | $CH_3$ | $CH_3$ | H | 3-methyl-2-chloropyridine | 4.04 94-98° C. |
| I-c-3 | 1 | H | $CH_3$ | $CH_3$ | $CH_3$ | H | 4-$CF_3$-5-methyl-2-methyl-thiazole | 4.66/4.71 |
| I-c-4 | 1 | H | $CH_3$ | $CH_3$ | $CH_3$ | H | 4-$CHF_2$-5-methyl-2-methyl-thiazole | 4.45/4.53 |
| I-c-5 | 1 | H | $CH_3$ | $CH_3$ | $CH_3$ | H | 3-methyl-2-chloropyrazine | 4.12/4.23 |
| I-c-6 | 1 | H | $CH_3$ | $CH_3$ | $CH_3$ | H | 3-$CF_3$-4-methyl-1-methyl-pyrazole | 4.10/4.53 |
| I-c-7 | 1 | H | $CH_3$ | $CH_3$ | $CH_3$ | H | 3-$CHF_2$-4-methyl-1-methyl-pyrazole | 3.88/4.28 |
| I-c-8 | 1 | H | $CH_3$ | $CH_3$ | $CH_3$ | H | 2-methyl-phenyl-$CF_3$ | 4.72/4.88 |
| I-c-9 | 1 | H | $CH_3$ | $CH_3$ | $CH_3$ | H | 3,4-dimethylthiophene | 4.73/5.15 |
| I-c-10 | 1 | H | $CH_3$ | $CH_3$ | $CH_3$ | H | 1,4-oxathiine-methyl, $CH_3$ | 4.52/4.83 |
| I-c-11 | 1 | H | $CH_3$ | $CH_3$ | $CH_3$ | H | 3-$CF_3$-4-methyl-1-methyl-pyrrole | 4.45/4.83 |
| I-c-12 | 1 | H | $CH_3$ | $CH_3$ | $CH_3$ | H | 3-methyl-2-methyl-furan | 4.27/4.58 |
| I-c-13 | 1 | H | $CH_3$ | $CH_3$ | $CH_3$ | H | 1,4-oxathiine-methyl, $CF_3$ | 4.49/4.67 |
| I-c-14 | 1 | H | $CH_3$ | $CH_3$ | $CH_3$ | H | 3,4-dimethyl-1-methyl-pyrazole | 3.18/3.47 |
| I-c-15 | 1 | H | $CH_3$ | $CH_3$ | $CH_3$ | H | 2-methyl-phenyl-I | 4.75/4.92 |
| I-c-16 | 1 | H | $CH_3$ | $CH_3$ | $CH_3$ | H | 2-methyl-phenyl-Cl | 4.60/4.83 |
| I-c-17 | 1 | H | $CH_3$ | $CH_3$ | $CH_3$ | H | 3-$CF_3$-4-methyl-5-fluoro-1-methyl-pyrazole | 4.49/4.75 |

TABLE 1-continued (I-c)

| No. | s | R¹ | R² | R³ | R⁴ | R⁵ | A | logP*/ m.p. (° C.) |
|---|---|---|---|---|---|---|---|---|
| I-c-18 | 1 | H | CH₃ | CH₃ | CH₃ | H | 2-Br-phenyl | 4.46/ 4.86 |
| I-c-19 | 1 | H | H | CH₃ | CH₃ | CH₃ | 3-CHF₂-1-methyl-4-methyl-pyrazole | 4.22 |
| I-c-20 | 1 | H | CH₃ | CH₃ | CH₃ | H | 2-CH₃-phenyl | 4.58/ 5.00 |
| I-c-21 | 1 | H | CH₃ | CH₃ | CH₃ | H | 3-CH₃-4-methyl-5-Cl-1-methyl-pyrazole | 4.10/ 4.43 |
| I-c-22 | 1 | H | CH₃ | CH₃ | CH₃ | H | 3-I-4-methyl-1-methyl-pyrazole | 3.9/ 4.32 |
| I-c-23 | 1 | H | H | CH₃ | CH₃ | CH₃ | 4-CHF₂-5-methyl-2-methyl-thiazole | 4.71 |
| I-c-24 | 1 | H | H | CH₃ | CH₃ | CH₃ | 3-CF₃-4-methyl-5-F-1-methyl-pyrazole | 4.72 |
| I-c-25 | 1 | H | H | CH₃ | CH₃ | CH₃ | 3-methyl-2-methyl-furan | 4.55 |
| I-c-26 | 1 | H | CH₃ | CH₃ | CH₃ | H | 3-methyl-2-methyl-dihydrofuran | 4.06 |
| I-c-27 | 1 | H | CH₃ | CH₃ | CH₃ | CH₃ | 2-methyl-3-Cl-pyrazine | 4.44/ 4.64 |
| I-c-28 | 1 | H | CH₃ | CH₃ | CH₃ | CH₃ | 3-I-4-methyl-1-methyl-pyrazole | 4.17/ 4.33/ 4.47/ 4.55 |
| I-c-29 | 1 | H | CH₃ | CH₃ | CH₃ | CH₃ | 2-CH₃-6-CF₃-phenyl | 4.94/ 4.98/ 5.08 |
| I-c-30 | 1 | H | CH₃ | CH₃ | CH₃ | CH₃ | 2-I-phenyl | 5.07/ 5.22 |
| I-c-31 | 1 | H | CH₃ | CH₃ | CH₃ | CH₃ | 3-methyl-2-methyl-dihydrofuran | 4.29/ 4.37/ 4.68 |
| I-c-32 | 1 | H | CH₃ | CH₃ | CH₃ | CH₃ | 3-methyl-2-methyl-thiophene | 4.97/ 5.07/ 5.36 |
| I-c-33 | 1 | H | CH₃ | CH₃ | CH₃ | CH₃ | 3-methyl-2-methyl-furan | 4.54/ 4.63/ 4.87 |
| I-c-34 | 1 | H | CH₃ | CH₃ | CH₃ | CH₃ | 3-CH₃-4-methyl-1-methyl-pyrazole | 3.42/ 3.54/ 3.66/ 3.74 |
| I-c-35 | 1 | H | CH₃ | CH₃ | CH₃ | CH₃ | 3-CF₃-4-methyl-1-methyl-pyrazole | 4.37/ 4.48/ 4.74/ 4.82 |

TABLE 1-continued (I-c)

A—C(=O)—N(R¹)—[cyclohexyl with Y¹ₙ]—CH(R²)—(CH₂)ₛ—C(R³)(R⁴)(R⁵)

| No. | s | R¹ | R² | R³ | R⁴ | R⁵ | A | logP*/m.p. (° C.) |
|---|---|---|---|---|---|---|---|---|
| I-c-36 | 1 | H | CH₃ | CH₃ | CH₃ | CH₃ | 4-methyl-3-(difluoromethyl)-1-methyl-pyrazol-5-yl | 4.15/ 4.27/ 4.48/ 4.57 |
| I-c-37 | 1 | H | CH₃ | CH₃ | CH₃ | CH₃ | 4-methyl-3-(trifluoromethyl)-1-methyl-pyrrol-5-yl | 4.70/ 4.80/ 5.11/ 5.16 |
| I-c-38 | 1 | H | CH₃ | CH₃ | CH₃ | CH₃ | 2-chloro-3-methylpyridin-yl | 4.15/ 4.21/ 4.35 |
| I-c-39 | 1 | H | H | CH₃ | CH₃ | CH₃ | 3-methyl-2-(trifluoromethyl)-1,4-oxathiin-yl | 4.66 |
| I-c-40 | 1 | H | H | CH₃ | CH₃ | CH₃ | 4-methyl-3-(trifluoromethyl)-1-methyl-pyrazol-5-yl | 4.45 |
| I-c-41 | 1 | H | H | CH₃ | CH₃ | CH₃ | 4-methyl-3-(trifluoromethyl)-1-methyl-pyrrol-5-yl | 4.88 |
| I-c-42 | 1 | H | H | CH₃ | CH₃ | CH₃ | 3-chloro-2-methylpyrazin-yl | 4.27 |
| I-c-43 | 1 | H | H | CH₃ | CH₃ | CH₃ | 3,4-dimethyl-1-methyl-pyrazol-5-yl | 3.29/ 3.42 |
| I-c-44 | 1 | H | CH₃ | CH₃ | CH₃ | CH₃ | 4-(difluoromethyl)-5-methyl-2-methyl-thiazol-yl | 4.73/ 4.83/ 5.08 |
| I-c-45 | 1 | H | CH₃ | CH₃ | CH₃ | CH₃ | 3,4-dimethyl-5-fluoro-1-methyl-pyrazol-yl | 4.04/ 4.19/ 4.36 |
| I-c-46 | 1 | H | CH₃ | CH₃ | CH₃ | CH₃ | 3-methyl-2-(trifluoromethyl)-1,4-oxathiin-yl | 4.78/ 4.86/ 4.95 |
| I-c-47 | 1 | H | CH₃ | CH₃ | CH₃ | CH₃ | 2,3-dimethyl-1,4-oxathiin-yl | 4.83/ 4.90/ 5.09/ 5.25 |
| I-c-48 | 1 | H | CH₃ | CH₃ | CH₃ | H | 3-methyl-2-iodothiophen-yl | 4.80/ 4.85/ 4.98/ 5.11 |
| I-c-49 | 1 | H | CH₃ | CH₃ | CH₃ | CH₃ | 4-methyl-3-(trifluoromethyl)-5-fluoro-1-methyl-pyrazol-yl | 4.77/ 4.85/ 5.00 |
| I-c-50 | 1 | H | CH₃ | CH₃ | CH₃ | CH₃ | 3-methyl-2-iodothiophen-yl | 5.03/ 5.11/ 5.40 |
| I-c-51 | 1 | H | CH₃ | CH₃ | CH₃ | CH₃ | 2-methylphenyl | 4.87/ 4.94/ 5.09 |
| I-c-52 | 1 | H | CH₃ | CH₃ | CH₃ | CH₃ | 2-chloro-3-methylphenyl | 4.91/ 5.11/ 5.16 |
| I-c-53 | 1 | H | CH₃ | CH₃ | CH₃ | CH₃ | 2-bromo-3-methylphenyl | 4.95/ 5.12/ 5.17 |

TABLE 1-continued (I-c)

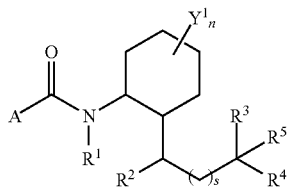

| No. | s | R¹ | R² | R³ | R⁴ | R⁵ | A | logP*/ m.p. (° C.) |
|---|---|---|---|---|---|---|---|---|
| I-c-54 | 1 | H | CH₃ | CH₃ | CH₃ | CH₃ | F₃C, CH₃ thiazole-CH₃ | 4.94/ 5.00/ 5.18 |
| I-c-55 | 1 | H | CH₃ | CH₃ | CH₃ | CH₃ | H₃C, CH₃ pyrazole-Cl, N-CH₃ | 4.36/ 4.52/ 4.70 |
| I-c-56 | 1 | H | H | CH₃ | CH₃ | H | F₃C, CH₃ thiazole-CH₃ | 4.6 |
| I-c-57 | 1 | H | H | CH₃ | CH₃ | H | F₃C, CH₃ pyrazole-N-CH₃ | 4.19 |
| I-c-58 | 1 | H | H | CH₃ | CH₃ | H | pyridine-CH₃, Cl | 3.76 |
| I-c-59 | 1 | H | H | CH₃ | CH₃ | H | F₂HC, CH₃ thiazole-CH₃ | 4.46 |
| I-c-60 | 1 | H | H | CH₃ | CH₃ | H | H₃C, CH₃ pyrazole-F, N-CH₃ | 3.79 |
| I-c-61 | 1 | H | H | CH₃ | CH₃ | H | phenyl-CH₃, CF₃ | 4.59 |

TABLE 1-continued (I-c)

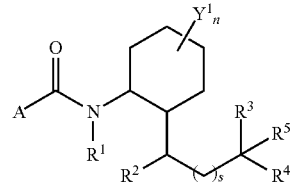

| No. | s | R¹ | R² | R³ | R⁴ | R⁵ | A | logP*/ m.p. (° C.) |
|---|---|---|---|---|---|---|---|---|
| I-c-62 | 1 | H | H | CH₃ | CH₃ | H | F₂HC, CH₃ pyrazole-N-CH₃ | 3.95 |
| I-c-63 | 1 | H | H | CH₃ | CH₃ | H | H₃C, CH₃ pyrazole-N-CH₃ | 3.19 |
| I-c-64 | 1 | H | H | CH₃ | CH₃ | H | S, CH₃ O-CF₃ dioxine | 4.42 |
| I-c-65 | 1 | H | H | CH₃ | CH₃ | H | furan-CH₃, CH₃ | 4.28 |
| I-c-66 | 1 | H | H | CH₃ | CH₃ | H | phenyl-CH₃, Br | 4.56 |
| I-c-67 | 1 | H | H | CH₃ | CH₃ | H | thiophene-CH₃, CH₃ | 4.82 |
| I-c-68 | 1 | H | H | CH₃ | CH₃ | H | S, CH₃ O-CH₃ dioxine | 4.51 |
| I-c-69 | 1 | H | H | CH₃ | CH₃ | H | F₃C, CH₃ pyrrole-N-CH₃ | 4.61 |
| I-c-70 | 1 | H | H | CH₃ | CH₃ | H | phenyl-CH₃, I | 4.66 |
| I-c-71 | 1 | H | H | CH₃ | CH₃ | H | phenyl-CH₃, Cl | 4.54 |

TABLE 1-continued
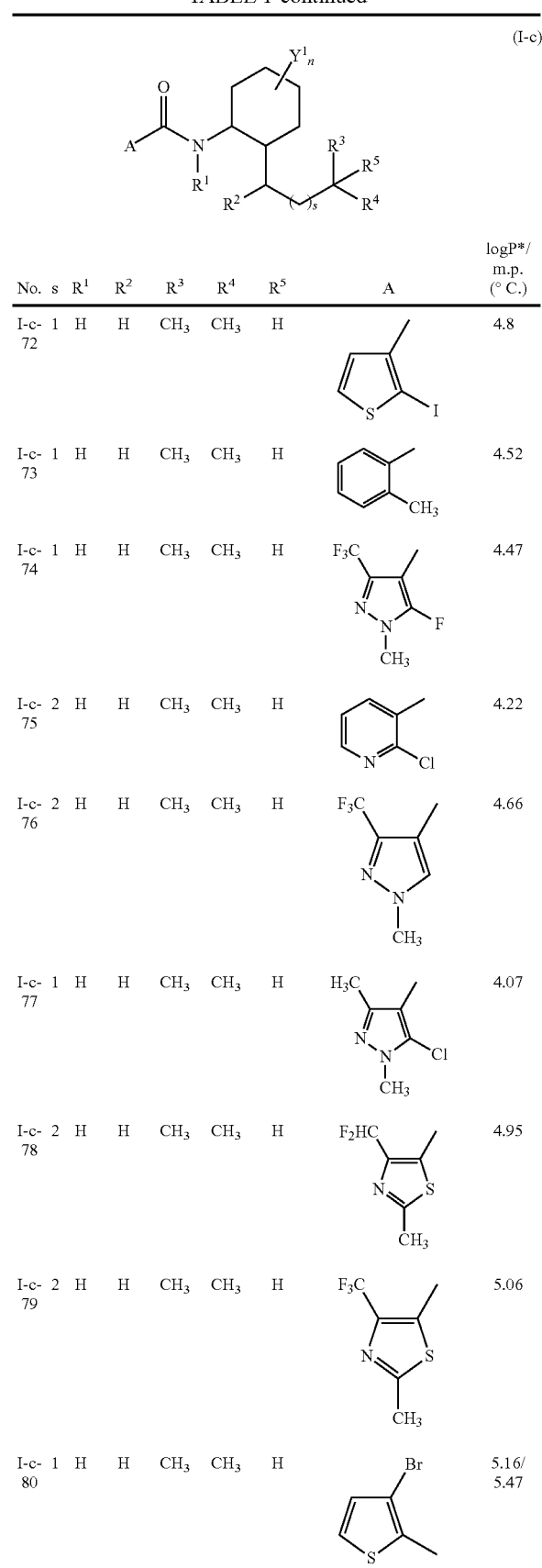
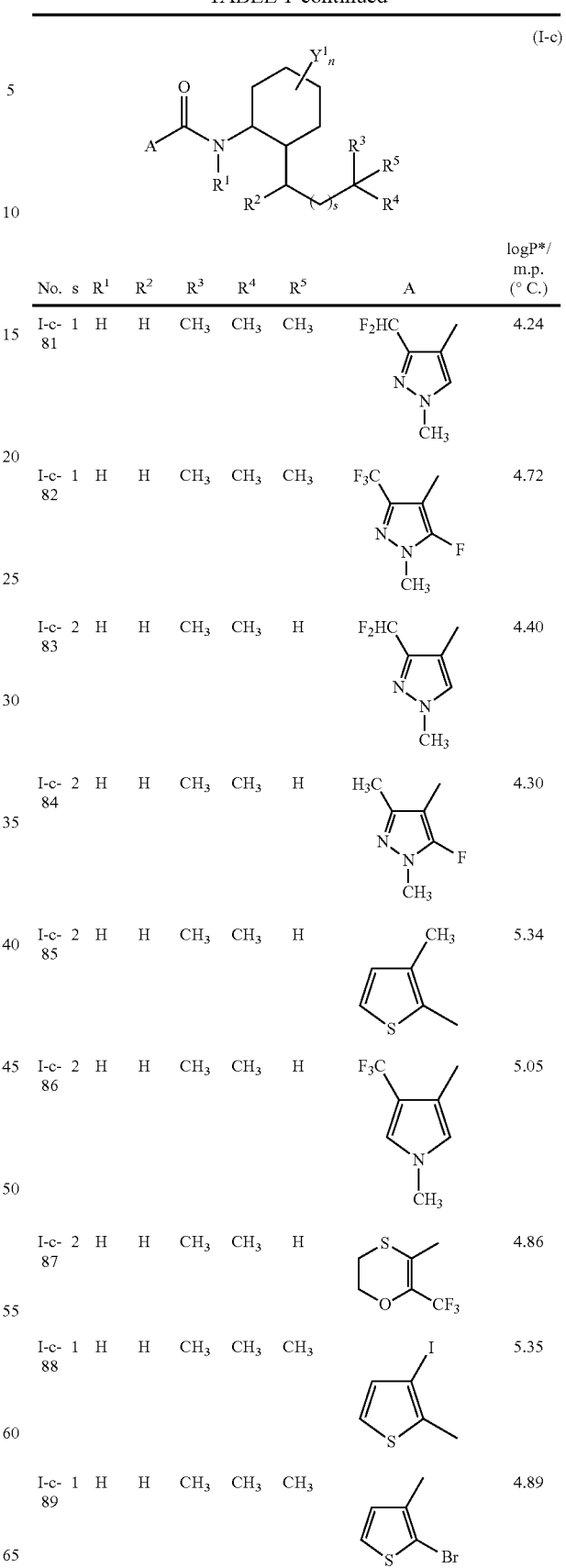

TABLE 1-continued (I-c)

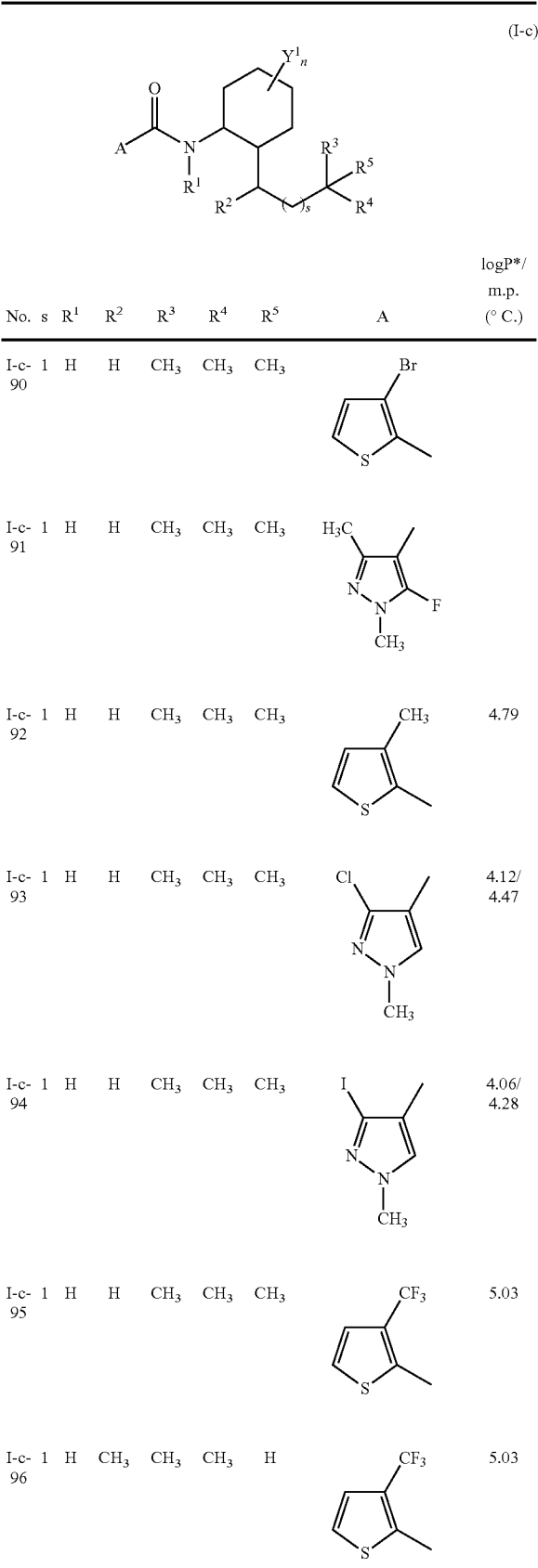

| No. | s | R¹ | R² | R³ | R⁴ | R⁵ | A | logP*/ m.p. (° C.) |
|---|---|---|---|---|---|---|---|---|
| I-c-90 | 1 | H | H | CH₃ | CH₃ | CH₃ | 3-Br-2-methylthiophene | |
| I-c-91 | 1 | H | H | CH₃ | CH₃ | CH₃ | 3,4-dimethyl-5-fluoro-1-methylpyrazole | |
| I-c-92 | 1 | H | H | CH₃ | CH₃ | CH₃ | 2,3-dimethylthiophene | 4.79 |
| I-c-93 | 1 | H | H | CH₃ | CH₃ | CH₃ | 3-chloro-4-methyl-1-methylpyrazole | 4.12/ 4.47 |
| I-c-94 | 1 | H | H | CH₃ | CH₃ | CH₃ | 3-iodo-4-methyl-1-methylpyrazole | 4.06/ 4.28 |
| I-c-95 | 1 | H | H | CH₃ | CH₃ | CH₃ | 3-CF₃-2-methylthiophene | 5.03 |
| I-c-96 | 1 | H | CH₃ | CH₃ | CH₃ | H | 3-CF₃-2-methylthiophene | 5.03 |

TABLE 1-continued (I-c)

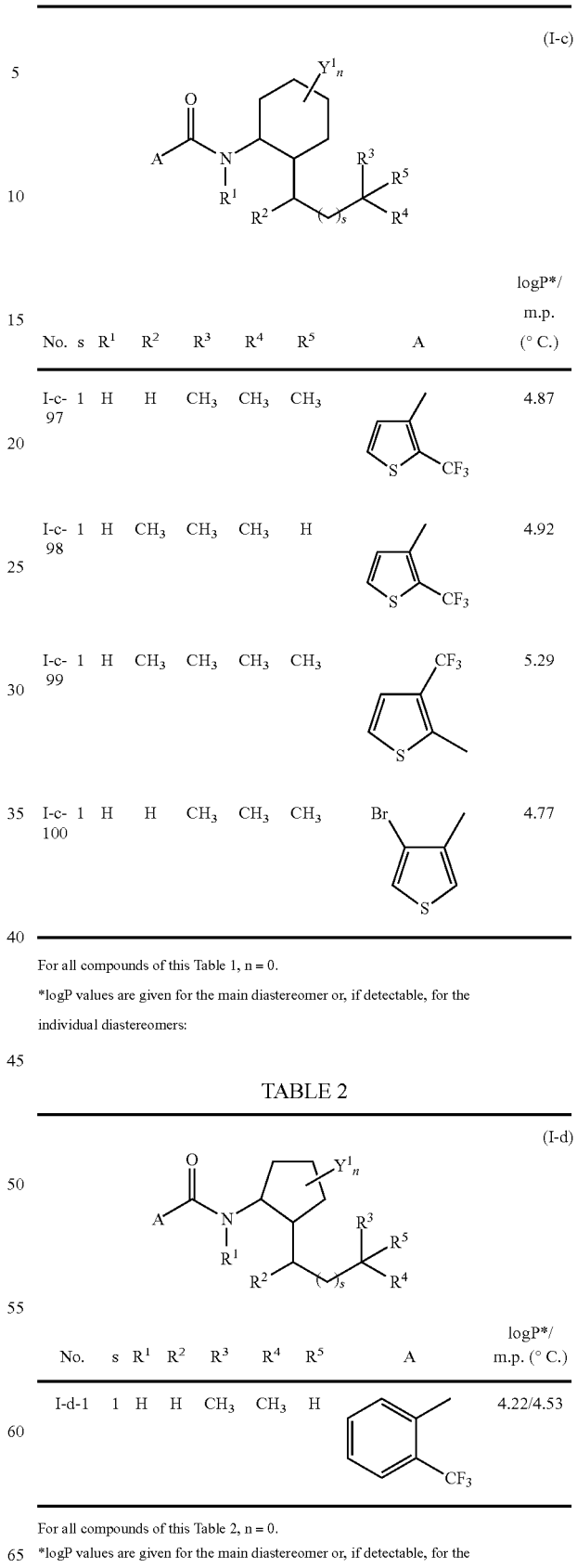

| No. | s | R¹ | R² | R³ | R⁴ | R⁵ | A | logP*/ m.p. (° C.) |
|---|---|---|---|---|---|---|---|---|
| I-c-97 | 1 | H | H | CH₃ | CH₃ | CH₃ | 3-methyl-2-CF₃-thiophene | 4.87 |
| I-c-98 | 1 | H | CH₃ | CH₃ | CH₃ | H | 3-methyl-2-CF₃-thiophene | 4.92 |
| I-c-99 | 1 | H | CH₃ | CH₃ | CH₃ | CH₃ | 3-CF₃-2-methylthiophene | 5.29 |
| I-c-100 | 1 | H | H | CH₃ | CH₃ | CH₃ | 3-Br-4-methylthiophene | 4.77 |

For all compounds of this Table 1, n = 0.

*logP values are given for the main diastereomer or, if detectable, for the individual diastereomers:

TABLE 2

(I-d)

| No. | s | R¹ | R² | R³ | R⁴ | R⁵ | A | logP*/ m.p. (° C.) |
|---|---|---|---|---|---|---|---|---|
| I-d-1 | 1 | H | H | CH₃ | CH₃ | H | 2-CF₃-phenyl | 4.22/4.53 |

For all compounds of this Table 2, n = 0.

*logP values are given for the main diastereomer or, if detectable, for the individual diastereomers:

TABLE 3

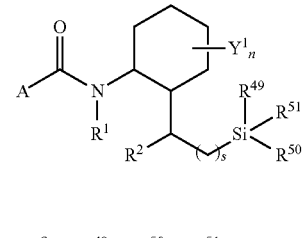

(I-k)

For all compounds of this Table 3, n = 0.
*the logP values are given for the main diastereomer or, if detectable, for the individual diastereomers:

| No. | s | R¹ | R² | R⁴⁹ | R⁵⁰ | R⁵¹ | A | logP*/m.p. (°C.) |
|---|---|---|---|---|---|---|---|---|
| I-k-1 | 1 | H | H | CH₃ | CH₃ | CH₃ | 3-methyl-4-methyl-1-methylpyrazol-5-yl (F) | 4.15 |
| I-k-2 | 1 | H | CH₃ | CH₃ | CH₃ | CH₃ | 3-methyl-4-methyl-1-methylpyrazol-5-yl (F) | 4.51 |
| I-k-3 | 1 | H | H | CH₃ | CH₃ | CH₃ | 3-methyl-2-iodothien-2-yl | 5.13 |
| I-k-4 | 1 | H | CH₃ | CH₃ | CH₃ | CH₃ | 3-methyl-2-iodothien-2-yl | 5.44 |
| I-k-5 | 1 | H | H | CH₃ | CH₃ | CH₃ | 3-difluoromethyl-4-methyl-1-methylpyrazol-5-yl | 4.25/4.54 |
| I-k-6 | 1 | H | CH₃ | CH₃ | CH₃ | CH₃ | 3-difluoromethyl-4-methyl-1-methylpyrazol-5-yl | 4.56 |
| I-k-7 | 1 | H | H | CH₃ | CH₃ | CH₃ | 3-difluoromethyl-4-methyl-2-methylthiazol-5-yl | 4.82/5.06 |
| I-k-8 | 1 | H | CH₃ | CH₃ | CH₃ | CH₃ | 3-difluoromethyl-4-methyl-2-methylthiazol-5-yl | 5.13 |

The stated log P values were determined in accordance with EEC Directive 79/831 Annex V. A8 by HPLC (High Performance Liquid Chromatography) on a reverse-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known log P values (determination of the log P values by the retention times using linear interpolation between two successive alkanones).

The lambda max values were determined in the maximum of the chromatographic signals using the UV spectra from 200 nm to 400 nm.

USE EXAMPLES

Example A

*Podosphaera* Test (Apple)/Protective

| Solvents: | 24.5 | parts by weight of acetone |
|---|---|---|
|  | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

TABLE A

Podosphaera test (apple)/protective

| Active compound according to the invention | | Application rate of active compound in g/ha | Efficacy in % |
|---|---|---|---|
| (I-c-4) | 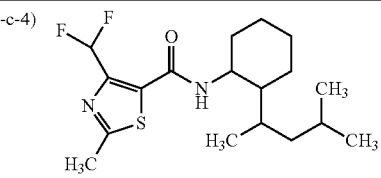 | 100 | 100 |
| (I-c-5) | 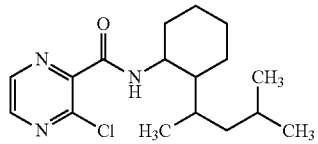 | 100 | 100 |
| (I-c-7) | 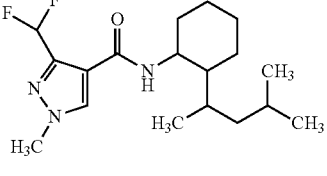 | 100 | 100 |
| (I-c-1) | 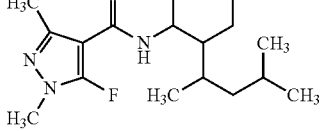 | 100 | 88 |

Example B

*Venturia* Test (Apple)/Protective

| Solvents: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabinet as about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE B

*Venturia* test (apple)/protective

| Active compound according to the invention | | Application rate of active compound in g/ha | Efficacy in % |
|---|---|---|---|
| (I-c-4) | 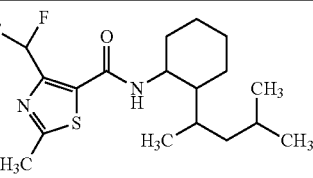 | 100 | 98 |
| (I-c-5) | 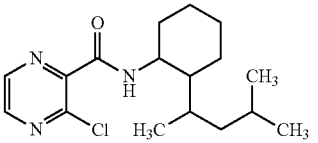 | 100 | 100 |
| (I-c-6) | 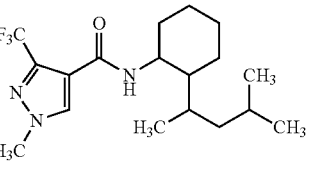 | 100 | 99 |
| (I-c-7) | 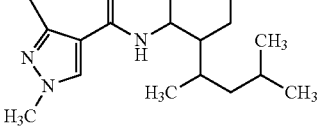 | 100 | 100 |
| (I-c-11) | 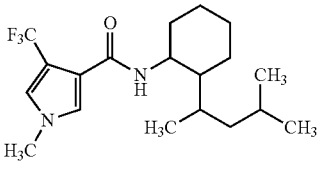 | 100 | 90 |
| (I-c-1) | 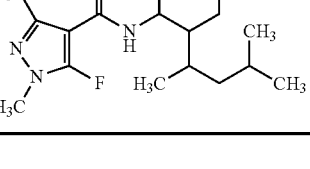 | 100 | 100 |

Example C

*Botrytis* Test (Bean)/Protective

| Solvents: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

TABLE C

*Botrytis* test (bean)/protective

| Active compound according to the invention | Application rate of active compound in g/ha | Efficacy in % |
|---|---|---|
| (I-c-4) | 500 | 95 |
| (I-c-5) | 500 | 99 |
| (I-c-6) | 500 | 90 |
| (I-c-7) | 500 | 94 |
| (I-c-11) | 500 | 96 |

Example D

*Puccinia* Test (Wheat)/Protective

| Solvent: | 50 | parts by weight of N,N-dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabinet at 20° C. and 100% relative atmospheric humidity for 48 hours. The plants are then placed in a greenhouse at a temperature of about 20° C. and a relative atmospheric humidity of 80%.

Evaluation is carried out 10 days after the inoculation. 0% means an efficacy which corresponds to that of the control, whereas an efficacy of 100% means that no infection is observed.

TABLE D

*Puccinia* test (wheat)/protective

| Active compound according to the invention | Application rate of active compound in g/ha | Efficacy in % |
|---|---|---|
| (I-c-3) | 500 | 100 |
| (I-c-4) | 500 | 100 |
| (I-c-14) | 500 | 100 |
| (I-c-5) | 500 | 100 |
| (I-c-6) | 500 | 100 |
| (I-c-7) | 500 | 100 |

TABLE D-continued

*Puccinia* test (wheat)/protective

| Active compound according to the invention | | Application rate of active compound in g/ha | Efficacy in % |
|---|---|---|---|
| (I-c-9) | 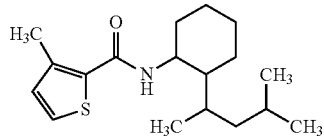 [SMILES: Cc1ccsc1C(=O)NC1CCCCC1C(C)CC(C)C] | 500 | 100 |
| (I-c-10) | 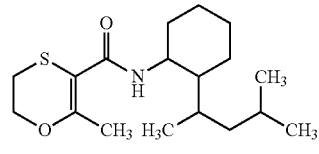 | 500 | 100 |
| (I-c-12) | 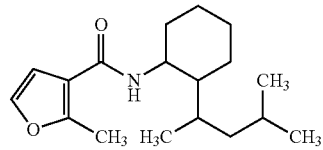 | 500 | 100 |
| (I-c-1) | 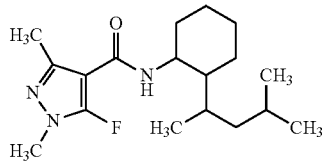 [SMILES: Cc1nn(C)c(F)c1C(=O)NC1CCCCC1C(C)CC(C)C] | 500 | 100 |

Example E

*Alternaria* Test (Tomato)/Protective

| Solvent: | 49 parts by weight of N,N-dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and then remain at 100% relative atmospheric humidity and 20° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

TABLE E

*Alternaria* test (tomato)/protective

| Active compound according to the invention | | Application rate of active compound in g/ha | Efficacy in % |
|---|---|---|---|
| (I-c-4) | 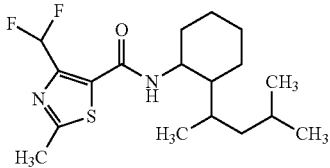 [SMILES: Cc1nc(C(F)F)c(C(=O)NC2CCCCC2C(C)CC(C)C)s1] | 750 | 100 |
| (I-c-14) | 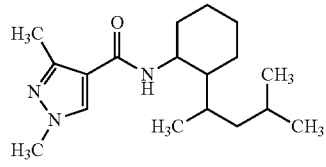 [SMILES: Cc1nn(C)cc1C(=O)NC1CCCCC1C(C)CC(C)C] | 750 | 100 |
| (I-c-5) | 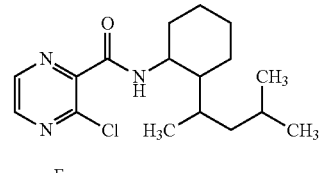 | 750 | 100 |
| (I-c-7) | 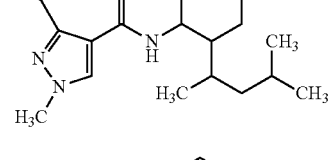 | 750 | 100 |
| (I-c-10) | 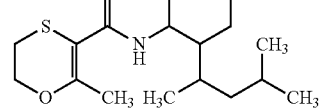 | 750 | 100 |

The invention claimed is:

1. A compound of the formula (I)

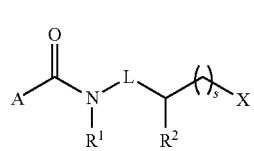

(I)

in which

X represents —CR$^3$R$^4$R$^5$, s represents 1 or 2,

R$^1$ represents hydrogen, C$_1$-C$_8$-alkyl, C$_1$-C$_6$-alkylsulphinyl, C$_1$-C$_6$-alkylsulphonyl, C$_1$-C$_4$-alkoxy-C$_1$-C$_4$-alkyl, C$_3$-C$_8$-cycloalkyl, C$_1$-C$_6$-haloalkyl, C$_1$-C$_4$-haloalkylthio, C$_1$-C$_4$-haloalkylsulphinyl, C$_1$-C$_4$-haloalkylsulphonyl, halo-C$_1$-C$_4$-alkoxy-C$_1$-C$_4$-alkyl, or C$_3$-C$_8$-halocycloalkyl, having in each case 1 to 9 fluorine, chlorine or bromine atoms;

represents formyl, formyl-C$_1$-C$_3$-alkyl, (C$_1$-C$_3$-alkyl)carbonyl-C$_1$-C$_3$-alkyl, or (C$_1$-C$_3$-alkoxy)carbonyl-C$_1$-C$_3$-alkyl;

represents halo-($C_1$-$C_3$-alkyl)carbonyl-$C_1$-$C_3$-alkyl, or halo-($C_1$-$C_3$-alkoxy)carbonyl-$C_1$-$C_3$-alkyl, having in each case 1 to 13 fluorine, chlorine or bromine atoms;

represents ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, or ($C_3$-$C_8$-cycloalkylcarbonyl;

represents ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, or ($C_3$-$C_8$-halocycloalkyl)carbonyl having in each case 1 to 9 fluorine, chlorine or bromine atoms; or represents —C(=O)C(=O)$R^6$, —CONR$^7$R$^8$ or —CH$_2$NR$^9$R$^{10}$, L represents

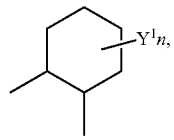

in which n represents 0, 1, 2, 3, or 4, $Y^1$ represents fluorine, chlorine, methyl, ethyl, n- or isopropyl, n-, iso-, sec- or tert-butyl, trifluoromethyl or difluoromethyl, wherein $Y^1$ is identical or different if n is greater than 1, $R^2$ represents hydrogen, halogen, $C_1$-$C_4$-alkyl or $C_1$-$C_4$-haloalkyl having 1 to 9 fluorine, chlorine or bromine atoms, $R^3$ represents halogen, $C_1$-$C_8$-alkyl or $C_1$-$C_6$-haloalkyl, having 1 to 13 fluorine, chlorine or bromine atoms, $R^4$ represents halogen, $C_1$-$C_8$-alkyl or $C_1$-$C_6$-haloalkyl, having 1 to 13 fluorine, chlorine or bromine atoms, $R^5$ represents hydrogen, halogen, $C_1$-$C_8$-alkyl or $C_1$-$C_6$-haloalkyl, having 1 to 13 fluorine, chlorine or bromine atoms, or $R^3$ and $R^4$ together with the carbon atom to which they are attached form a 3- to 6-membered carbocyclic, heterocyclic, saturated or unsaturated ring, each of which is optionally substituted by halogen, $C_1$-$C_4$-alkyl, $C_1$-$C_4$-alkoxy, $C_1$-$C_4$-haloalkyl or $C_1$-$C_4$-haloalkoxy, $R^6$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl, $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl, having in each case 1 to 9 fluorine, chlorine or bromine atoms, $R^7$ and $R^8$ independently of one another each represent hydrogen, $C_1$-$C_8$-alkyl, $C_1$-$C_4$-alkoxy-$C_1$-$C_4$-alkyl, or $C_3$-$C_8$-cycloalkyl, halo-$C_1$-$C_4$-alkoxy-$C_1$-$C_4$-alkyl, or $C_3$-$C_8$-halocycloalkyl, having in each case 1 to 9 fluorine, chlorine or bromine atoms, or $R^7$ and $R^8$ together with the nitrogen atom to which they are attached form a saturated heterocycle having 5 to 8 ring atoms which is optionally mono- or polysubstituted by identical or different substituents selected from the group consisting of halogen and $C_1$-$C_4$-alkyl, where the heterocycle optionally further contains 1 or 2 non-adjacent heteroatoms selected from the group consisting of oxygen, sulphur and NR$^{11}$, $R^9$ and $R^{10}$ independently of one another represent hydrogen, $C_1$-$C_8$-alkyl, or $C_3$-$C_8$-cycloalkyl;

represents $C_1$-$C_8$-haloalkyl or $C_3$-$C_8$-halocycloalkyl, having in each case 1 to 9 fluorine, chlorine or bromine atoms, or $R^9$ and $R^{10}$ together with the nitrogen atom to which they are attached form a saturated heterocycle having 5 to 8 ring atoms which is optionally mono- or polysubstituted by identical or different substituents selected from the group consisting of halogen and $C_1$-$C_4$-alkyl, where the heterocycle optionally further contains 1 or 2 non-adjacent heteroatoms selected from the group consisting of oxygen, sulphur and NR$^{11}$, $R^{11}$ represents hydrogen or $C_1$-$C_6$-alkyl, A represents a radical of the formula (A2)

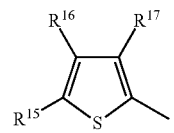
(A2)

in which $R^{15}$ and $R^{16}$ independently of one another represent hydrogen, halogen, $C_1$-$C_4$-alkyl or $C_1$-$C_4$-haloalkyl having 1 to 5 halogen atoms, $R^{17}$ represents halogen, cyano or $C_1$-$C_4$-alkyl; or represents $C_1$-$C_4$-haloalkyl or $C_1$-$C_4$-haloalkoxy having in each case 1 to 5 halogen atoms, or A represents a radical of the formula (A3)

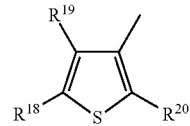
(A3)

in which $R^{18}$ and $R^{19}$ independently of one another represent hydrogen, halogen, $C_1$-$C_4$-alkyl or $C_1$-$C_4$-haloalkyl having 1 to 5 halogen atoms, $R^{20}$ represents hydrogen, halogen, $C_1$-$C_4$-alkyl or $C_1$-$C_4$-haloalkyl, having 1 to 5 halogen atoms, or A represents a radical of the formula (A4)

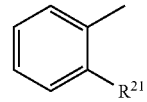
(A4)

in which $R^{21}$ represents hydrogen, halogen, hydroxyl, cyano, $C_1$-$C_4$-haloalkyl, $C_1$-$C_4$-haloalkoxy or $C_1$-$C_4$-haloalkylthio, having in each case 1 to 5 halogen atoms, or
A represents a radical of the formula (A6)

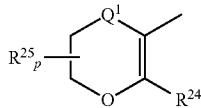
(A6)

in which
R$^{24}$ represents C$_1$-C$_4$-alkyl or C$_1$-C$_4$-haloalkyl having 1 to 5 halogen atoms,
R$^{25}$ represents C$_1$-C$_4$ alkyl,
Q$^1$ represents S (sulphur), O (oxygen), SO, SO$_2$ or CH$_2$,
p represents 0, 1 or 2,
provided that when p is 2, R$^{25}$ represents identical different radicals,
or
A represents a radical of the formula (A7)

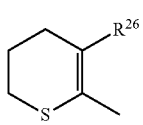
(A7)

in which
R$^{26}$ represents C$_1$-C$_4$-alkyl or C$_1$-C$_4$-haloalkyl having 1 to 5 halogen atoms,
or
A represents a radical of the formula (A8)

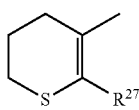
(A8)

in which
R$^{27}$ represents C$_1$-C$_4$-alkyl or C$_1$-C$_4$-haloalkyl having 1 to 5 halogen atoms,
or
A represents a radical of the formula (A9)

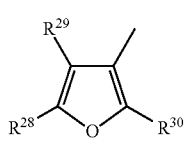
(A9)

in which
R$^{28}$ and R$^{29}$ independently of one another represent hydrogen, halogen, amino, C$_1$-C$_4$-alkyl or C$_1$-C$_4$-haloalkyl, having 1 to 5 halogen atoms,
R$^{30}$ represents hydrogen, halogen, C$_1$-C$_4$-alkyl or C$_1$-C$_4$-haloalkyl having 1 to 5 halogen atoms, or
A represents a radical of the formula (A 10)

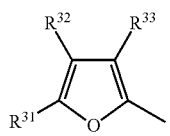
(A10)

in which
R$^{31}$ and R$^{32}$ independently of one another represent hydrogen, halogen, amino, nitro, C$_1$-C$_4$-alkyl or C$_1$-C$_4$-haloalkyl having 1 to 5 halogen atoms,
R$^{33}$ represents hydrogen, halogen, C$_1$-C$_4$-alkyl or C$_1$-C$_4$-haloalkyl having 1 to 5 halogen atoms,
or
A represents a radical of the formula (A11)

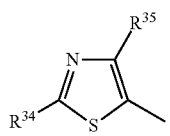
(A11)

in which
R$^{34}$ represents hydrogen, halogen, amino, C$_1$-C$_4$-alkylamino, di-(C$_1$-C$_4$ alkyl)amino, cyano, C$_1$-C$_4$-alkyl or C$_1$-C$_4$-haloalkyl having 1 to 5 halogen atoms,
R$^{35}$ represents halogen, C$_1$-C$_4$-alkyl or C$_1$-C$_4$-haloalkyl having 1 to 5 halogen atoms,
or
A represents a radical of the formula (A12)

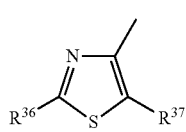
(A12)

in which
R$^{36}$ represents hydrogen, halogen, amino, C$_1$-C$_4$-alkylamino, di-(C$_1$-C$_4$-alkyl)amino, cyano, C$_1$-C$_4$-alkyl or C$_1$-C$_4$-haloalkyl having 1 to 5 halogen atoms,
R$^{37}$ represents halogen, C$_1$-C$_4$-alkyl or C$_1$-C$_4$-haloalkyl having 1 to 5 halogen atoms,
or
A represents a radical of the formula (A13)

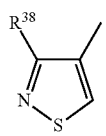
(A13)

in which
R$^{38}$ represents halogen, C$_1$-C$_4$-alkyl or C$_1$-C$_4$-haloalkyl having 1 to halogen atoms, or A represents a radical of the formula (A14)

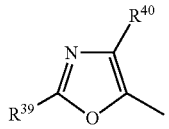
(A14)

in which
R$^{39}$ represents hydrogen or C$_1$-C$_4$-alkyl,
R$^{40}$ represents halogen or C$_1$-C$_4$-alkyl,
or
A represents a radical of the formula (A18)

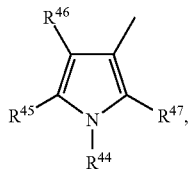
(A18)

in which
R$^{44}$ represents hydrogen, cyano, C$_1$-C$_4$-haloalkyl having 1 to 5 halogen atoms, C$_1$-C$_4$-alkoxy-C$_1$-C$_4$-alkyl, hydroxy-C$_1$-C$_4$-alkyl, C$_1$-C$_4$-alkylsulphonyl, di(C$_1$-C$_4$-alkyl)aminosulphonyl, C$_1$-C$_6$-alkylcarbonyl, or in each case optionally substituted phenylsulphonyl or benzoyl,
R$^{45}$ represents hydrogen, halogen, C$_1$-C$_4$-alkyl or C$_1$-C$_4$-haloalkyl having 1 to 5 halogen atoms,
R$^{46}$ represents hydrogen, halogen, cyano, C$_1$-C$_4$-alkyl or C$_1$-C$_4$-haloalkyl having 1 to 5 halogen atoms,
R$^{47}$ represents hydrogen, halogen, C$_1$-C$_4$-alkyl or C$_1$-C$_4$-haloalkyl having 1 to 5 halogen atoms,
or
A represents a radical of the formula (A19)

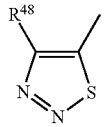
(A19)

in which
R$^{48}$ represents C$_1$-C$_4$-alkyl.

2. A process for preparing the compound according to claim 1, comprising reacting
(a) a carboxylic acid derivative of the formula (II)

(II)

in which
A is as defined in claim 1 and
X$^1$ represents halogen or hydroxyl,
with an aniline derivative of the formula (III)

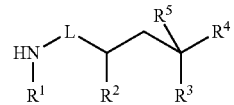
(III)

in which
R$^1$, L, R$^2$, R$^3$, R$^4$ and R$^5$ are as defined in claim 1,
optionally in the presence of a catalyst, optionally in the presence of a condensing agent, optionally in the presence of an acid binder and optionally in the presence of a diluent, or
(b) a compound of the formula (I-a)

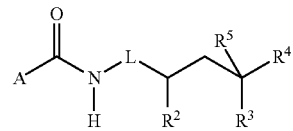
(I-a)

in which
L, R$^2$, R$^3$, R$^4$, R$^5$ and A are as defined in claim 1,
with a halide of the formula (IV)

$$R^{14}-X^2 \quad (IV)$$

in which
R$^{14}$ represents C$_1$-C$_8$-alkyl, C$_1$-C$_6$-alkylsulphinyl, C$_1$-C$_6$-alkylsulphonyl, C$_1$-C$_4$-alkoxy-C$_1$-C$_4$-alkyl, or C$_3$-C$_8$-cycloalkyl;
represents C$_1$-C$_6$-haloalkyl, C$_1$-C$_4$-haloalkylthio, C$_1$-C$_4$-haloalkylsulphinyl, C$_1$-C$_4$-haloalkylsulphonyl, halo-C$_1$-C$_4$-alkoxy-C$_1$-C$_4$-alkyl, or C$_3$-C$_8$-halocycloalkyl, having in each case 1 to 9 fluorine, chlorine or bromine atoms;
represents formyl, formyl-C$_1$-C$_3$-alkyl, (C$_1$-C$_3$-alkyl)-carbonyl-C$_1$-C$_3$-alkyl, (C$_1$-C$_3$-alkoxy)carbonyl-C$_1$-C$_3$-alkyl, halo-(C$_1$-C$_3$-alkyl)carbonyl-C$_1$-C$_3$-alkyl or halo-(C$_1$-C$_3$-alkoxy)carbonyl-C$_1$-C$_3$-alkyl, having in each case 1 to 13 fluorine, chlorine or bromine atoms;
represents (C$_1$-C$_8$-alkyl)carbonyl, (C$_1$-C$_8$-alkoxy)carbonyl, (C$_1$-C$_4$-alkoxy-C$_1$-C$_4$-alkyl)-carbonyl, (C$_3$-C$_8$-cycloalkyl)carbonyl, (C$_1$-C$_6$-haloalkyl)carbonyl, (C$_1$-C$_6$-haloalkoxy)carbonyl, (halo-C$_1$-C$_4$-alkoxy-C$_1$-C$_4$-alkyl)carbonyl, or (C$_3$-C$_8$-halocycloalkyl)carbonyl, having in each case 1 to 9 fluorine, chlorine or bromine atoms; or
represents —C(=O)C(=O)R$^6$, —CONR$^7$R$^8$ or —CH$_2$NR$^9$R$^{10}$,
R$^6$, R$^7$, R$^8$, R$^9$ and R$^{10}$ are as defined in claim 1,
X$^2$ represents chlorine, bromine or iodine,
in the presence of a base and a diluent.

3. A composition for controlling unwanted microorganisms, comprising at least one compound according to claim 1, and an extender, a surfactant, or a combination thereof.

4. A method for controlling unwanted microorganisms, comprising applying 2-alkylcycloalk(en)ylcarboxamides of the formula (I) according to claim 1 to plants and plant parts directly or to their environment, habitat, or store.

5. A method for controlling unwanted microorganisms, comprising contacting a compound according to claim 1 with the microorganisms or their habitat.

6. A process for preparing compositions for controlling unwanted microorganisms, comprising mixing a compound according to claim 1 with an extender, a surfactant or a combination thereof.

7. The compound of the formula (I) according to claim 1, wherein $R^1$ represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, or C(=O)CO$_2$CH$_2$CH$_3$, $R^2$ represents hydrogen, fluorine, chlorine, methyl, ethyl, or trifluoromethyl, $R^3$ represents chlorine, methyl, ethyl, isopropyl, or trifluoromethyl, $R^4$ represents chlorine, methyl, ethyl, isopropyl, or trifluoromethyl, and $R^5$ represents hydrogen, chlorine, methyl, ethyl, isopropyl, or trifluoromethyl.

8. The compound according to claim 1 is Compound I-c-4:

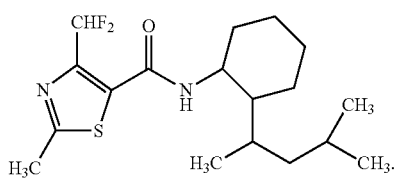 [SMILES: Cc1nc(C(F)F)c(C(=O)NC2CCCCC2C(C)CC(C)C)s1]

9. The method for controlling unwanted microorganisms according to claim 5, wherein the compound is Compound I-c-4:

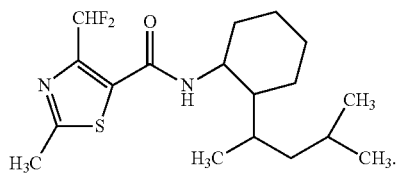 [SMILES: Cc1nc(C(F)F)c(C(=O)NC2CCCCC2C(C)CC(C)C)s1]

10. The process for preparing the composition according to claim 6, wherein the compound is Compound I-c-4:

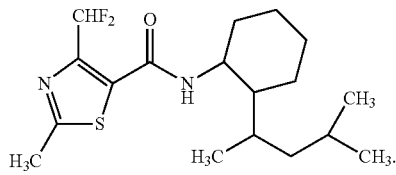 [SMILES: Cc1nc(C(F)F)c(C(=O)NC2CCCCC2C(C)CC(C)C)s1]

* * * * *